(12) United States Patent
Gerstner et al.

(10) Patent No.: US 7,420,674 B2
(45) Date of Patent: Sep. 2, 2008

(54) METHOD AND ARRANGEMENT FOR ANALYZING SAMPLES

(75) Inventors: Volker Gerstner, Jena (DE); Joerg Lindenau, Jena (DE)

(73) Assignee: Carl Zeiss MicroImaging GmbH, Jena (DE)

( * ) Notice: Subject to any disclaimer, the term of this patent is extended or adjusted under 35 U.S.C. 154(b) by 285 days.

(21) Appl. No.: 10/514,673

(22) PCT Filed: May 14, 2003

(86) PCT No.: PCT/EP03/05033

§ 371 (c)(1),
(2), (4) Date: Nov. 16, 2004

(87) PCT Pub. No.: WO03/098313

PCT Pub. Date: Nov. 27, 2003

(65) Prior Publication Data

US 2005/0179892 A1  Aug. 18, 2005

(30) Foreign Application Priority Data

May 16, 2002 (DE) .............................. 102 22 779

(51) Int. Cl.
*G01J 3/30* (2006.01)
(52) U.S. Cl. .................. 356/318; 356/317; 356/417; 250/458.1; 250/461.2
(58) Field of Classification Search ............... 356/317, 356/318, 417, 458.1, 461.2, 459.1; 250/458.1, 250/461.2, 459.1
See application file for complete search history.

(56) References Cited

U.S. PATENT DOCUMENTS 5,510,894 A  4/1996 Batchelder et al.

(Continued)

FOREIGN PATENT DOCUMENTS

DE  197 02 753  7/1998

(Continued)

OTHER PUBLICATIONS

Pawley, "Handbook of Biological Confocal Microscopy"; Plenum Press 1995.

(Continued)

*Primary Examiner*—Gregory J Toatley, Jr.
*Assistant Examiner*—Abdullahi Nur
(74) *Attorney, Agent, or Firm*—Reed Smith LLP

(57) ABSTRACT

A method and/or arrangement for the analysis of fluorescing samples in an image-generating microscope system, preferably a laser scanning microscope, wherein the sample is scanned point-by-point or line-by-line in at least one surface section and a dispersive splitting of the radiation coming from the sample is carried out during the scanning, wherein the split radiation is detected by at least one line of detector elements in a wavelength-dependent manner, a selection of two-dimensional or three-dimensional sample parts which correspond to pre-stored two-dimensional or three-dimensional geometric objects or the like is carried out based on the recorded and stored intensity distribution of at least one of these detection elements and/or at least one other detection element for the radiation reflected from the sample by image processing, and an analysis of the spectral signature and/or spatial spectral sequence is carried out for at least a portion of these sample regions with respect to the fluorescence markers arranged thereon.

3 Claims, 20 Drawing Sheets

U.S. PATENT DOCUMENTS

| | | | | |
|---|---|---|---|---|
| 5,784,162 A | * | 7/1998 | Cabib et al. | 356/456 |
| 5,936,731 A | | 8/1999 | Cabib et al. | |
| 7,064,813 B2 | * | 6/2006 | Takahashi et al. | 356/73 |
| 2002/0044272 A1 | * | 4/2002 | Basiji et al. | 356/73 |
| 2002/0180965 A1 | * | 12/2002 | Engelhardt et al. | 356/318 |

FOREIGN PATENT DOCUMENTS

| | | |
|---|---|---|
| DE | 197 13 362 | 10/1998 |
| DE | 198 35 072 | 2/2000 |
| DE | 198 42 288 | 2/2000 |
| DE | 198 59 314 | 6/2000 |
| DE | 100 38 526 | 2/2002 |
| DE | 100 38 528 | 2/2002 |
| DE | 100 33 180 | 5/2002 |
| WO | WO 02/01222 | 1/2002 |

OTHER PUBLICATIONS

Corle, Kino, "Confocal Scanning, Optical Microscopy and Related Imaging Systems"; Academic Press 1996.

"Flow Cytometry and Sorting", second edition, M. R. Melamed, T. Lindmo, M. L. Mendelsohn, eds., Wiley & Sons, Inc., New York, 1990, pp. 81-107.

PCA, I.T. Joliffe, *Principal Component Analysis*, Springer-Verlag, New York, 1986.

Chemical Analysis, vol. 137, Chapter 4, pp. 87-124"Spectral Bio-Imaging" Y. Garini, et al.

XP002257573: Zeiss Brochure (online) Nov. 2000(200-11), "Anonymous: Cell Observer: Leben mit neuen Augen sehen".

XP02257574: Phys. Med. Biol (online) 1996, pp. 523-537 "Automated cell cycle analysis with fluorescence microscopy and image analysis" W. Buecker, et al.

XP002257575: Zeiss News (online) May 2002, pag 1-2, Anonymous: Particle Analyser: Schnelle Durchfuehrung Dokumentations- und Messaufgaben.

XP002257576: Zeiss Brochure (online), Anonymous: Particle Analyser—Die Funktionen.

* cited by examiner

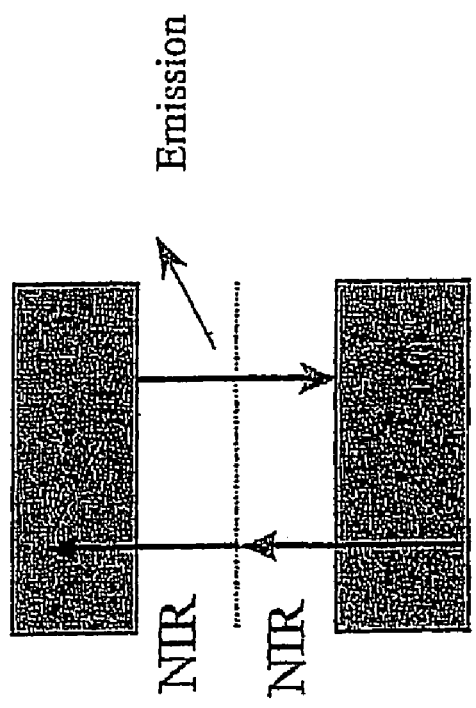
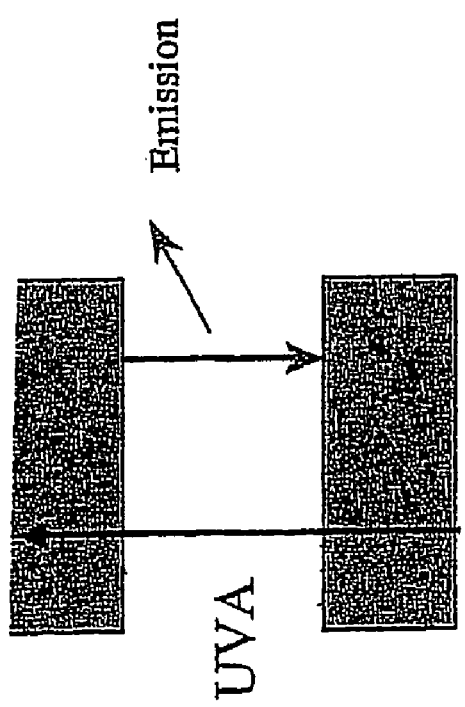
Fig. 1

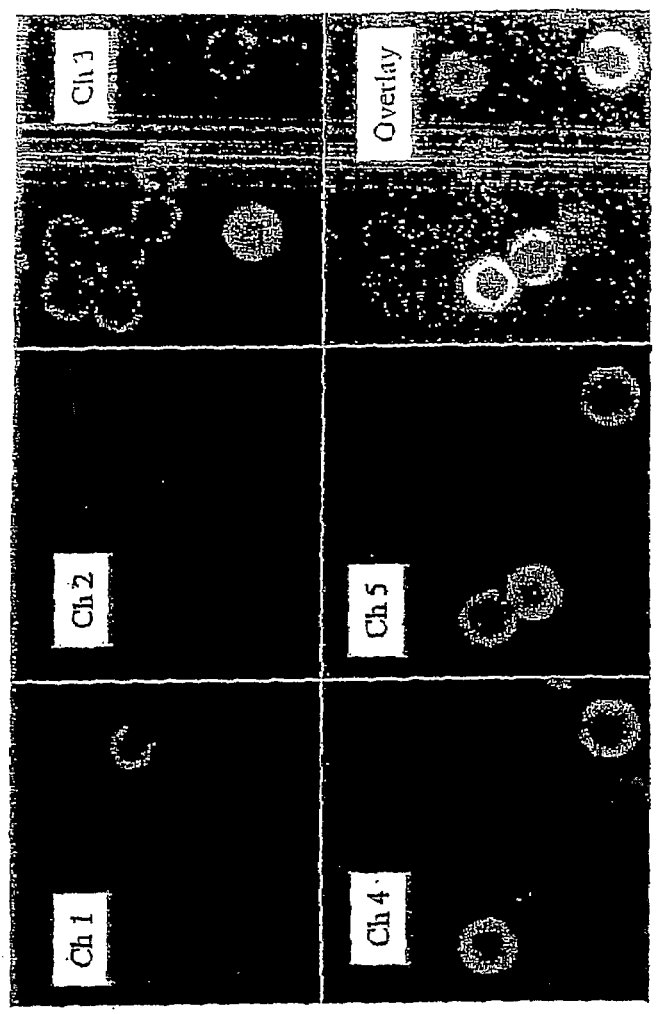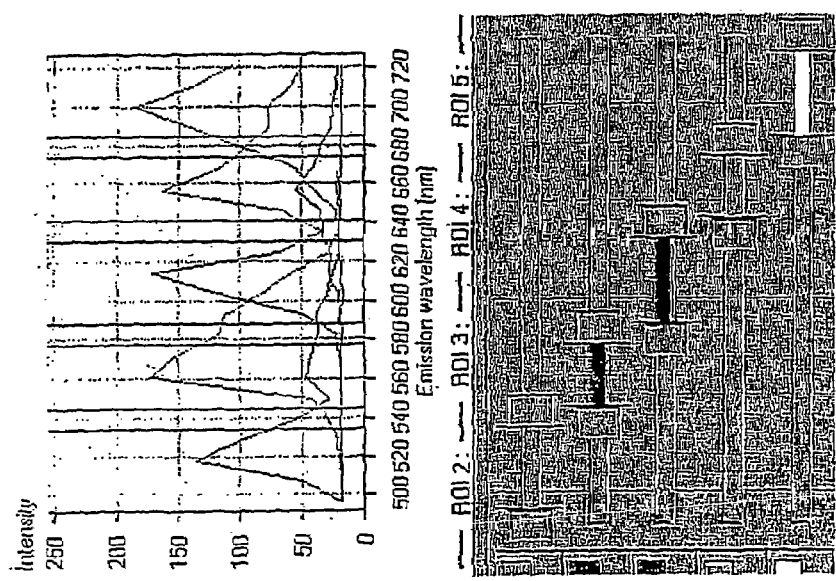
Fig. 9

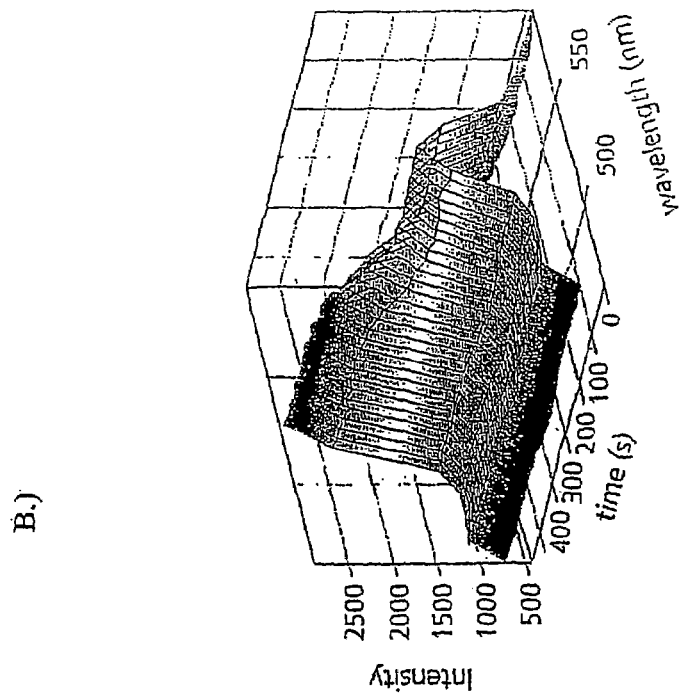
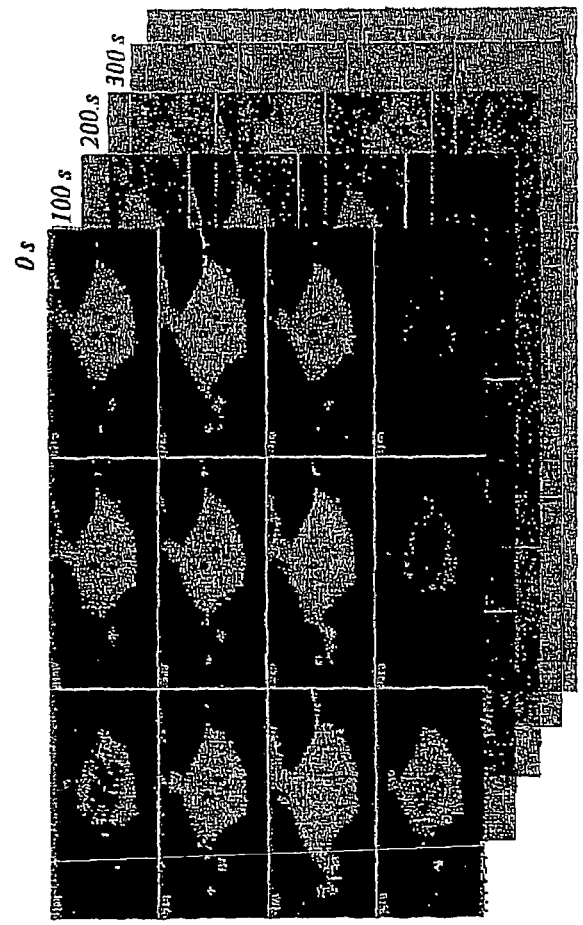
Fig. 10

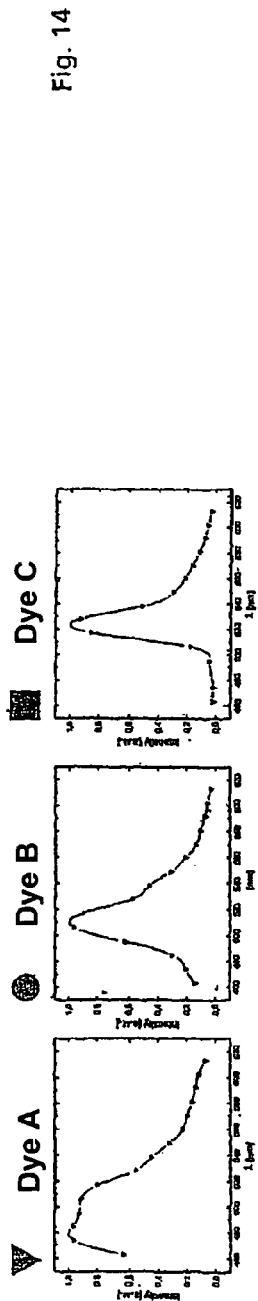
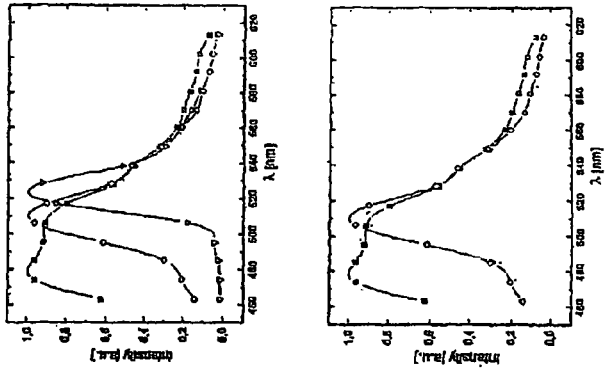
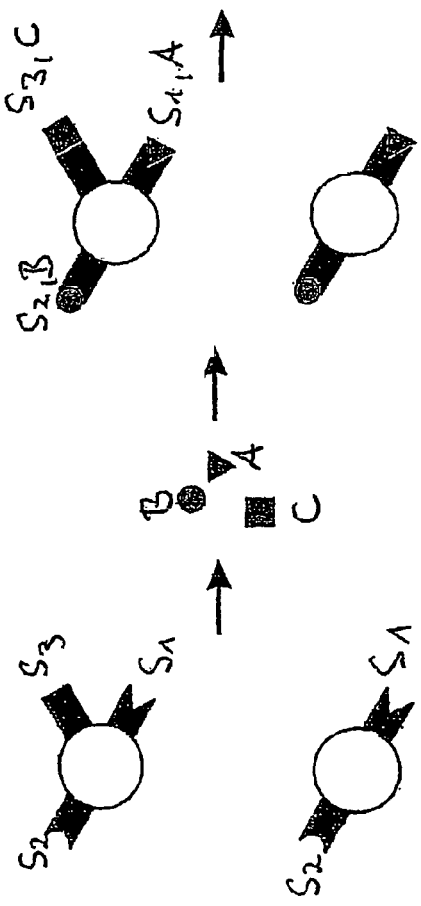
Fig. 14

METHOD AND ARRANGEMENT FOR ANALYZING SAMPLES

CROSS-REFERENCE TO RELATED APPLICATIONS

This application claims priority of PCT Application Serial No. PCT/EP03/05033, filed May 14, 2003 and German Application No. 102 22 779.9, filed May 16, 2002, the complete disclosures of which are hereby incorporated by reference.

BACKGROUND OF THE INVENTION a) Field of the Invention

The invention is directed to a method in fluorescence microscopy, particularly laser scanning microscopy, for analyzing predominantly biological samples, preparations and associated components. Included are methods based on fluorescence detection, e.g., fluorescence correlation microscopy, methods for screening active ingredients (high throughput screening), total internal reflection fluorescence microscopy (TIRF), and nearfield scanning microscopy.

The transition from the detection of a few broad-spectrum dye bands to the simultaneous acquisition of whole spectra opens up new possibilities for the identification, separation and correlation of mostly analytic or functional sample characteristics. These include spectral, spatial and dynamic characteristics or combinations of these characteristics. Simultaneous analyses of many types of markings of chromosomes (multicolor banding (MCB) and FISH or related techniques) can be carried out in metaphase and interphase samples for scientific or diagnostic purposes.

Through the simultaneous detection of complete spectra, the detection efficiency is substantially increased compared to prior art methods. The resulting increase in sensitivity makes it possible to detect smaller dye concentrations and/or reduced intensity of the excitation light that it used. In this way, the bleaching effects and toxic effects of excitation can be minimized.

b) Description of the Related Art

A typical area of application of light microscopy for examining biological preparations is fluorescence microscopy (Pawley, "Handbook of Biological Confocal Microscopy"; Plenum Press 1995). In this case, determined dyes are used for specific labeling of cell parts.

The irradiated photons having a determined energy excite the dye molecules, through the absorption of a photon, from the ground state to an excited state. This excitation is usually referred to as single-photon absorption (FIG. 1a). The dye molecules excited in this way can return to the ground state in various ways. In fluorescence microscopy, the most important transition is by emission of a fluorescence photon. Because of the Stokes shift, there is generally a red shift in the wavelength of the emitted photon in comparison to the excitation radiation; that is, it has a greater wavelength. Stokes shift makes it possible to separate the fluorescence radiation from the excitation radiation.

The fluorescent light is split off from the excitation radiation by suitable dichroic beam splitters in combination with blocking filters and is observed separately. This makes it possible to show individual cell parts that are dyed with different dyes. In principle, however, multiple parts of a preparation can also be dyed simultaneously with different dyes which bind in a specific manner (multiple fluorescence). Special dichroic beam splitters are used again to distinguish the fluorescence signals emitted by the individual dyes.

In addition to excitation of dye molecules with a high-energy photon (single-photon absorption), excitation with a plurality of lower-energy photons is also possible (FIG. 1b). The sum of energies of the single photons corresponds approximately to a multiple of the high-energy photon. This type of excitation of dyes is known as multiphoton absorption (Corle, Kino, "Confocal Scanning, Optical Microscopy and Related Imaging Systems"; Academic Press 1996). However, the dye emission is not influenced by this type of excitation, i.e., the emission spectrum undergoes a negative Stokes shift in multiphoton absorption; that is, it has a smaller wavelength compared to the excitation radiation. The separation of the excitation radiation from the emission radiation is carried out in the same way as in single-photon excitation.

The prior art will be described in the following by way of example with reference to a confocal laser scanning microscope (LSM) (FIG. 2).

An LSM is essentially composed of four modules: light source, scan module, detection unit and microscope. These modules are described more fully in the following. In addition, reference is had to DE19702753A1.

Lasers with different wavelengths are used in an LSM for specific excitation of different dyes in a preparation. The choice of excitation wavelength is governed by the absorption characteristics of the dyes to be examined. The excitation radiation is generated in the light source module. Various lasers (argon, argon-krypton, helium-neon, solid state lasers, diode lasers, Ti:Sa lasers, etc.) are used for this purpose. Further, the selection of wavelengths and the adjustment of the intensity of the required excitation wavelength is carried out in the light source module, e.g., using an acousto-optic crystal. The laser radiation subsequently reaches the scan module via a fiber or a suitable mirror arrangement.

The laser radiation generated in the light source is focused in the sample in a diffraction-limited manner by the objective through the scanner, scan optics and tube lens. The scanner scans the sample in a point raster in x-y direction. The pixel dwell times when scanning over the sample are mostly in the range of less than one microsecond to several seconds.

In confocal detection (descanned detection) of fluorescent light, the light emitted from the focal plane (specimen) and from the planes located above and below the latter reaches a dichroic beam splitter (MDB) via the scanner. This dichroic beam splitter separates the fluorescent light from the excitation light. The fluorescent light is subsequently focused on a diaphragm (confocal diaphragm/pinhole) located precisely in a plane conjugate to the focal plane. In this way, fluorescent light components that were generated outside of the focus are suppressed. The optical resolution of the microscope can be adjusted by varying the diameter of the diaphragm. Another dichroic blocking filter (emission filter EF) which again suppresses the excitation radiation is located behind the diaphragm. After passing the blocking filter, the fluorescent light is measured by means of a point detector (PMT).

When using multiphoton absorption, the excitation of the dye fluorescence is carried out in a small volume in which the excitation intensity is particularly high. This area is only negligibly larger than the detected area when using a confocal arrangement. Accordingly, a confocal diaphragm can be dispensed with and detection can be carried out directly following the objective (nondescanned detection).

In another arrangement for detecting a dye fluorescence excited by multiphoton absorption, descanned detection is carried out again, but this time the pupil of the objective is imaged in the detection unit (descanned detection).

In a sample extending in three dimensions, only the plane of the sample (optical section) located in the focal plane of the objective is reproduced by the two detection arrangements in connection with corresponding single-photon absorption or multiphoton absorption. By recording a plurality of optical sections in the x-y plane at different depths z of the sample, a three-dimensional image of the sample can be generated subsequently in a computer-assisted manner.

Accordingly, the LSM is suitable for examination of thick preparations. Different fluorescence dyes are characterized by different absorption spectra and emission spectra. The laser lines for exciting the dye or dyes are selected in accordance with the absorption spectra. Dichroic filters adapted to the emission characteristics of the dye or dyes ensure that only the fluorescent light emitted by the respective dye will be measured by the point detector.

Currently, in biomedical applications, a plurality of different cell regions are labeled simultaneously by different dyes (multifluorescence). In the prior art, the individual dyes can be detected separately based either on different absorption characteristics or on emission characteristics (spectra) (FIG. 3a). FIG. 3a shows the emission spectra of different typical dyes. The intensity of the emission is plotted as a function of wavelength. It will be noted that the dyes designated by 1 to 4 differ with respect to the position and shape of their emission spectra.

According to the prior art, existing methods known in the art for spectral splitting of emission signals can be divided into two categories:

A Sequential Data Acquisition:
1) Combination of a spectrally dispersive element with monochromatic detection
2) Methods of interferometric spectroscopy
3) Multitracking, i.e., change in excitation wavelength according to image or line recording for separating dyes with different absorption characteristics (reference to our application)

B Parallel Data Acquisition:
1) Spectral splitting of the fluorescence emission by means of secondary color splitting and emission filtration.

Methods A1 and B3 are applied in the LSM 510 laser scanning microscope by Zeiss.

Flow cytometers are used for analyzing and classifying cells and other particles. For this purpose, the samples are dissolved or suspended in a liquid and are pumped through a capillary. In order to examine the samples, a laser beam is focused in the capillary from the side. The samples are labeled with different dyes or fluorescing biomolecules. The fluorescence emission and the scattered excitation light are measured. The art is described in "Flow Cytometry and Sorting", second edition, M. R. Melamed, T. Lindmo, M. L. Mendelsohn, eds., Wiley & Sons, Inc., New York, 1990, pp 81-107.

The size of the samples can be determined from the scattered signal. Different sample particles can be separated and/or sorted or counted separately by means of the spectral characteristics of the fluorescence of individual samples. The sorting of the sample particles is carried out with an electrostatic field in different collecting vessels. The evaluation of this technique is carried out by means of histograms which provide information about the intensities of the labeling and about the quantity of differently labeled samples. The through-flow rate is typically about 10-100 cm/s. Therefore, a highly sensitive detection is necessary. According to the prior art, a confocal detection is carried out in order to limit the detection volume.

The accuracy of the through-flow measurement is influenced by different factors. Such factors are, for example, nonspecific fluorescence, autofluorescence of cells, fluorescence of optical components and the noise of the detectors that are used.

Disadvantages of the Methods of the Prior Art

Dyes with sharply overlapping excitation and emission spectra can hardly be separated from one another without crosstalk. This problem becomes more severe as the quantity of fluorescence dyes to be detected increases. Therefore, a unique correlation of the emission of a dye to a detection channel is impossible. Yet this is absolutely necessary for accurate assessment in the analysis of multiply labeled samples.

Other troublesome and unwanted effects in multifluorescence recordings are superimposed background signals. These background signals can be reflections of individual lasers at the sample or broadband autofluorescence signals of sample constituents that overlap the spectral signatures of the fluorescence-labeled sample locations to be analyzed and therefore make it difficult and sometimes even impossible to analyze these sample locations.

Chromosomes that are labeled with up to seven different dyes by means of multicolor banding technique, FISH or related techniques pose special demands for the detection and separation of the individual markings. Samples of this kind can be analyzed according to the prior art by all of the methods listed above under A and B. These methods have the following disadvantages:

In B1, the spectral splitting of fluorescence emissions by means of secondary color splitting and emission filtration, the emission spectra intersect increasingly as the quantity of dyes increases. This results in crosstalk. Accordingly, it is impossible to uniquely correlate the emission of a dye to a detection channel.

Method A3 (multitracking) only solves the problem when the excitation spectra are sufficiently different from one another. However, this is not the case when a plurality of dyes are used.

Methods A1 (combination of a spectrally dispersive element with monochromatic detection) and A2 (interferometric spectroscopy) are, in themselves, likewise incapable of solving the problem of overlapping emission spectra. However, they are suitable for detecting the spectra information at a sample point.

The combination of methods A1 and A2 with a mathematical algorithm for unmixing overlapping spectra is suitable, in principle, for solving the problem described above (Schäfer application, ASI application). Both methods have the disadvantage of low efficiency compared to the invention described hereinafter. In method A1, only a narrow spectral band is detected at the detection time interval. A plurality of successive measurements are needed to detect a spectrum. This reduces the signal-to-noise ratio of the measurement. Further, repeated illumination of the samples with excitation light damages the fluorescence dyes and the samples themselves (e.g., through phototoxic processes).

In interferometric methods (A2), the detection efficiency is reduced to 50% based on theoretical considerations (citation). In order to acquire spectra from the raw data, a Fourier transform is required. For this purpose, the data are typically subjected to a digital Fourier transform (DFT) or, in case of a quantity of $2^n$ data points, to a fast Fourier transform (FFT). The computing time required for these calculations is not negligible.

SUMMARY OF THE INVENTION

A method and/or arrangement for the analysis of fluorescing samples in an image-generating microscope system, preferably a laser scanning microscope system, wherein the sample is scanned point-by-point or line-by-line in at least one surface section. A dispersive splitting of the radiation coming from the sample is carried out during the scanning. The split radiation is detected by at least one line of detector elements in a wavelength-dependent manner. A selection of two-dimensional or three-dimensional sample parts which correspond to pre-stored two-dimensional or three-dimensional geometric objects or the like is carried out based on the recorded and stored intensity distribution of at least one of said detection elements and/or at least one other detection element by image processing. An analysis of the spectral signature and/or spatial spectral sequence is carried out for at least a portion of these sample regions with respect to the fluorescent markers arranged thereon.

BRIEF DESCRIPTION OF THE DRAWINGS

In the drawings:

FIG. 1a illustrates single-photon absorption in graphical representation;

FIG. 1b illustrates multiple-photon absorption with a plurality of lower energy photons;

FIG. 9 illustrates how the spectral signatures of the different ROIs can be used to generate a color-coded multichannel image;

FIG. 10 illustrates a three-dimensional display for visualizing data;

FIG. 14 illustrates how information contained in the sample is coded exclusively by the proportional combination of different dyes;

DESCRIPTION OF THE PREFERRED EMBODIMENTS

Figure 2:
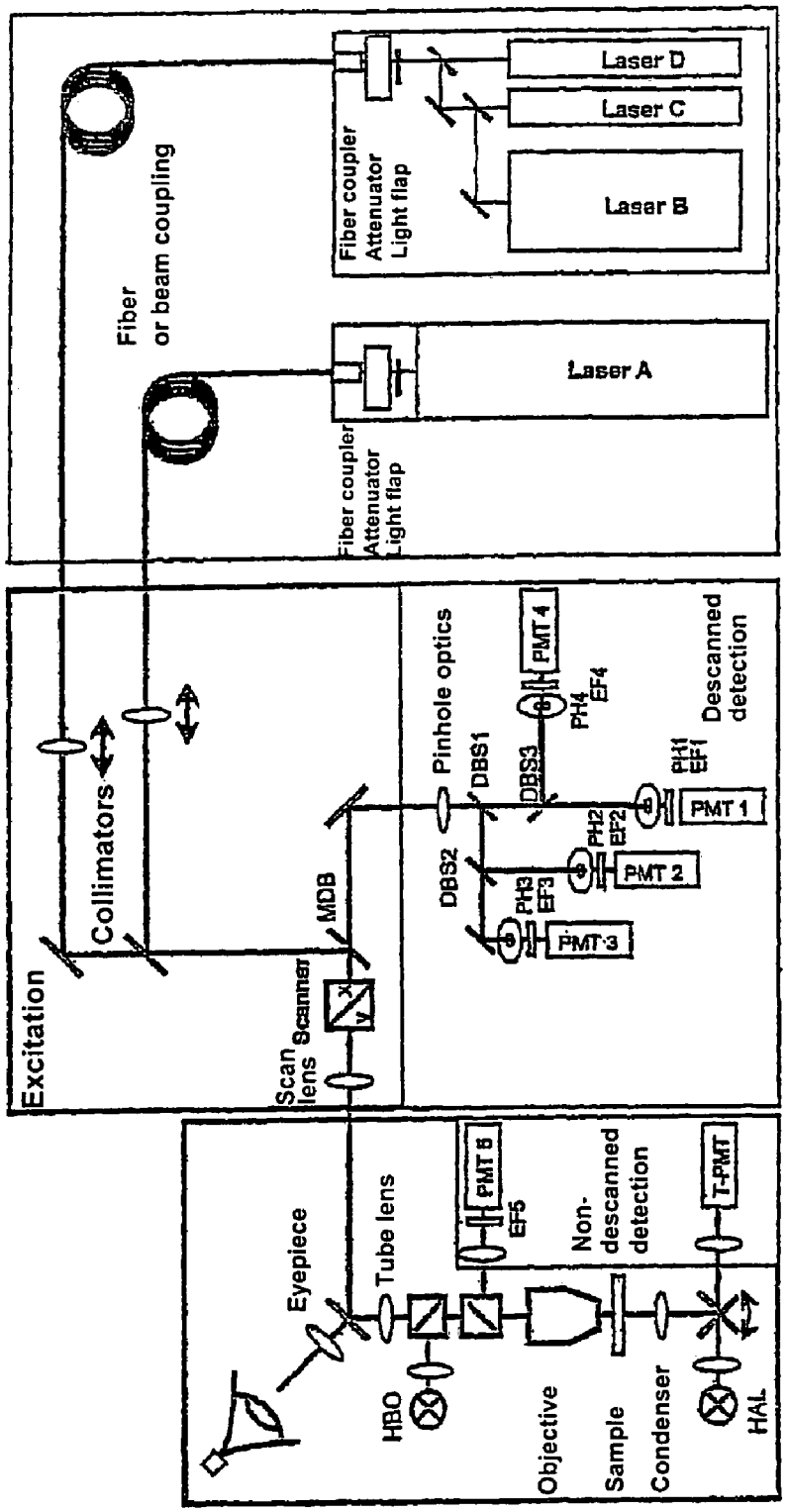
FIG. 2 is a schematic representation of a confocal laser scanning microscope.
Figure 3:
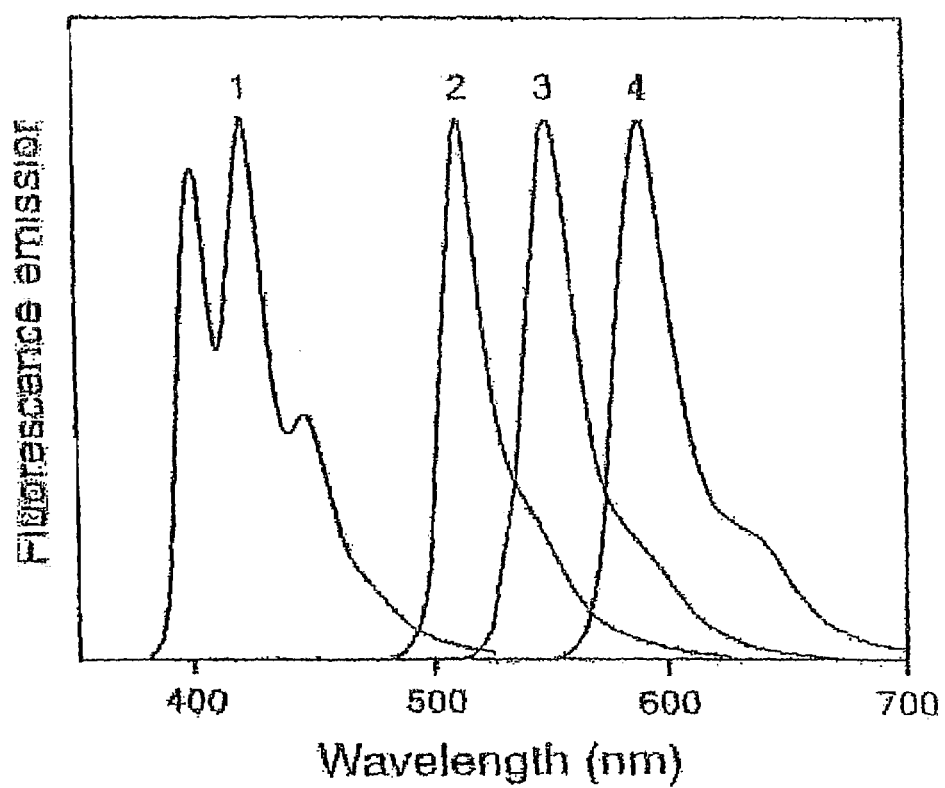
FIG. 3a shows the emission spectra of different typical dyes.
Figure 4:
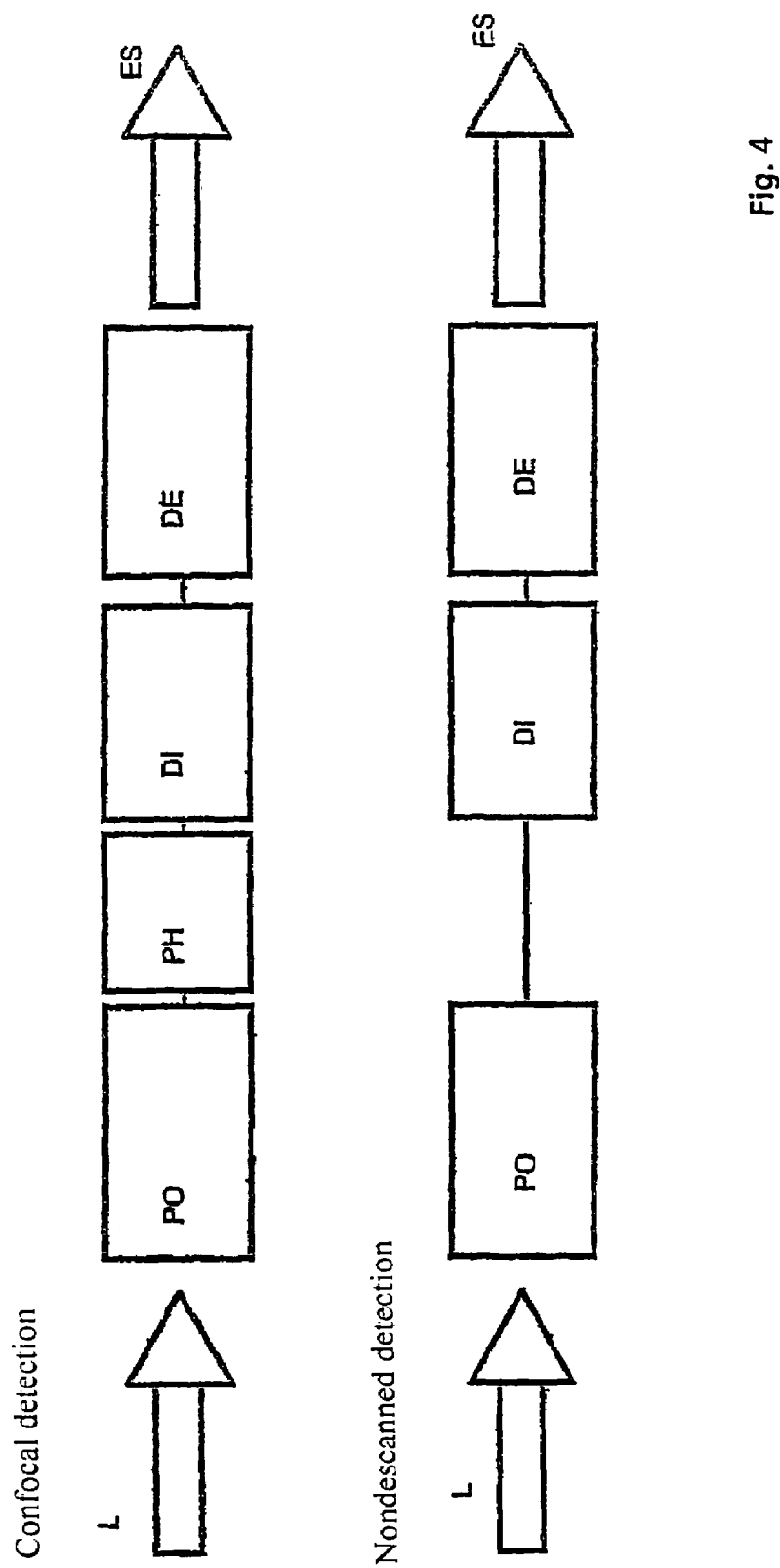
FIG. 4 illustrates, in block diagram form, a detector unit.

The background of the method according to the invention is a spectrally split detection of fluorescence. For this purpose, the emission light is split from the excitation light in the scan module or in the microscope (with multiphoton absorption) by means of an element for separating the excitation radiation from the detected radiation such as the main color splitter (main dichroic beam splitter (MDB)) or an AOTF according to DE19859314 A1 or DE 19842288. With transmitted-light arrangements, this type of element can also be entirely omitted. A block diagram of the detector unit to be described in the following is shown in FIG. 4. With confocal detection, the light from the sample L is focused through a diaphragm (pinhole) PH by means of imaging optics PO, so that fluorescence occurring outside of the focus is suppressed. In nondescanned detection, the diaphragm is omitted. The light is now divided into its spectral components by an angle-dispersive element DI. The angle-dispersive elements can be prisms, gratings and, e.g., acousto-optic elements. The light which is split into its spectral components by the dispersive element is subsequently imaged on a line detector DE. This line detector DE measures the emission signal as a function of wavelength and converts it into electrical signals S. In addition, a line filter for suppressing the excitation wavelengths can be arranged in front of the detection unit. Different variants are shown in FIG. 5 (supplement filter wheel plus diaphragm in FIG. 5).

Figure 5:
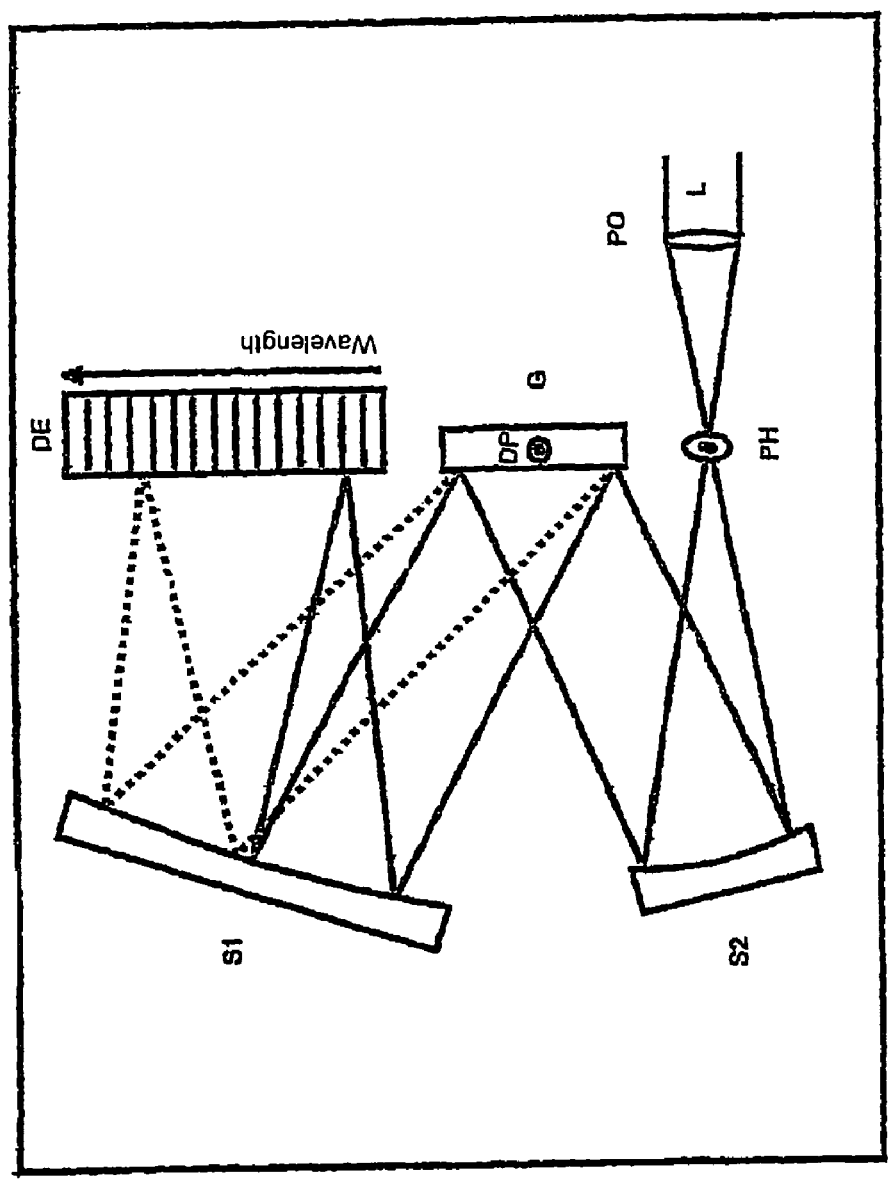
FIG. 5 illustrates an embodiment form of the optical beam path of the detector unit shown in the block diagram of FIG. 4.

FIG. 5 shows a possible embodiment form of the optical beam path of the detector unit shown in the block diagram in FIG. 4. The construction is essentially a Czerny-Turner construction. In confocal detection, the light L of the sample is focused through the confocal diaphragm PH by the pinhole optics PO. With nondescanned detection in case of multiphoton absorption, this diaphragm can be omitted. The first imaging mirror S2 collimates the fluorescent light. Subsequently, the light strikes a line grating G, for example, a grating with a line number of 651 lines per mm. The grating bends the light in different directions corresponding to its wavelength. The second imaging mirror S1 focuses the individual spectrally split wavelength components on the corresponding channels of the line detector DE. The use of a secondary electron multiplier array, e.g., Hamamatsu H7260, is especially advantageous. The detector has 32 channels and a high sensitivity. The free spectral region of the embodiment form described above is approximately 350 nm. In this arrangement, the free spectral region is uniformly distributed to the 32 channels of the line detector resulting in a resolution of approximately 10 nm. Therefore, this arrangement is suitable for spectroscopy only conditionally. However, its use in an image-generating system is advantageous because the signal per detection channel is still relatively large due to the relatively broad detected spectral band. A shift of the free spectral region can be carried out in addition, for example, by rotating the grating by DP.

In the embodiment form(s) described above, each individual channel of the detector DE detects a spectral band of the emission spectrum with a spectral width of approximately 10 nm. The sum of the spectral components of the individual dyes at the image point that has just been measured is recorded for each image point.

Figure 6:
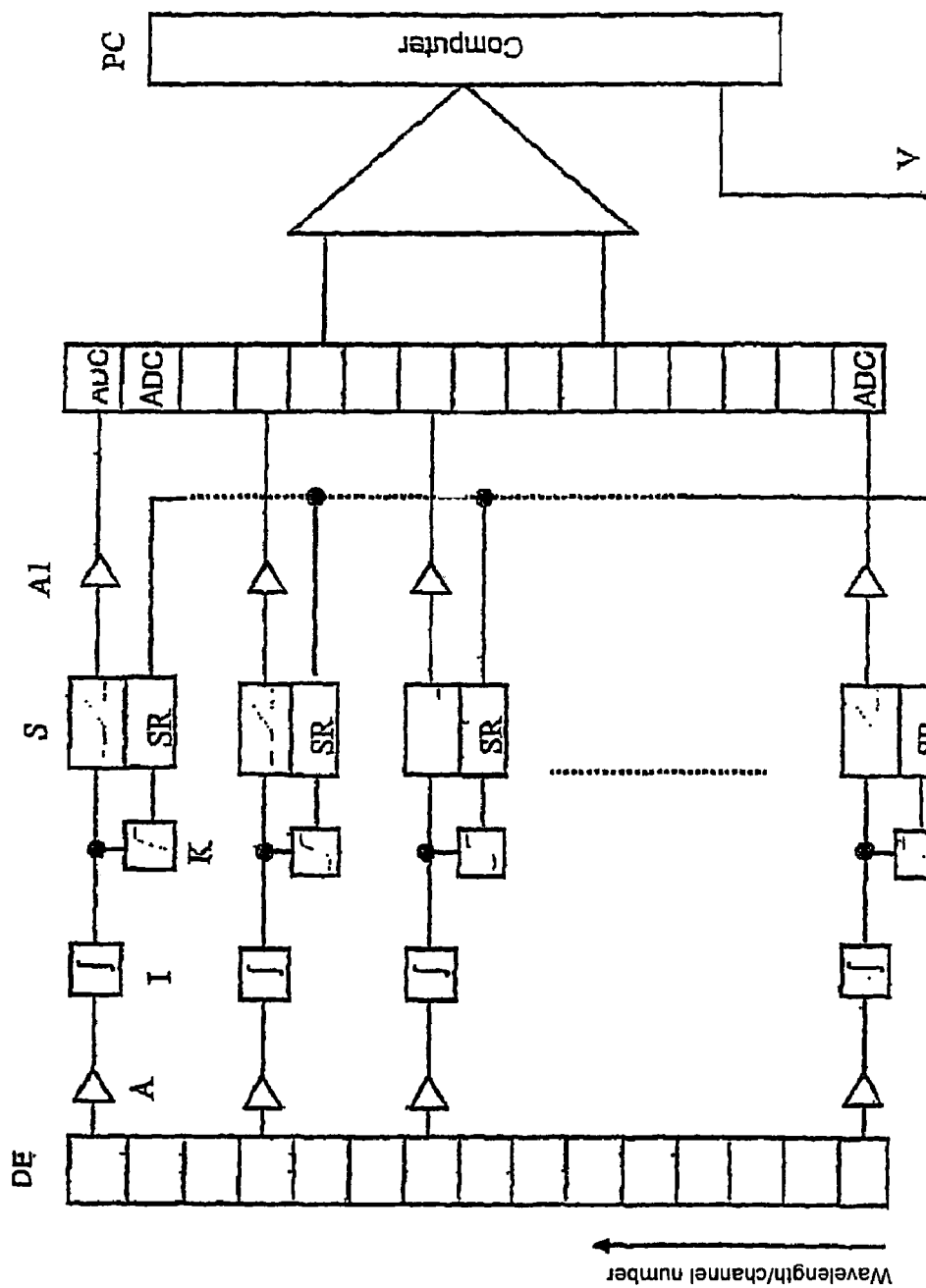
FIG. 6 shows an arrangement for reading out the individual channels of the detector unit DE shown in FIG. 5.

An arrangement for reading out the individual channels of the detector DE is shown schematically in FIG. 6. In this case, the current at the anode of a multichannel PMT (detector DE) is converted to voltage and amplified through the first amplifier A (connected as current-voltage converter). The voltage is fed to an integrator I which integrates the signal over a corresponding time period (e.g., pixel dwell time).

For faster evaluation, the integrator I can be followed by a comparator K which, as a simple comparator, has a switching threshold such that a digital output signal is generated when this threshold is exceeded or which is constructed as a window comparator and then forms a digital output signal when the input signal lies between the upper and lower switching threshold or when the input signal lies outside (below or above) the switching thresholds. The comparator or window comparator can be arranged before as well as after the integrator. Circuit arrangements without an integrator (so-called amplifier mode) are also possible. With the amplifier mode arrangement, the comparator K is still also provided after corresponding level matching. The output of the comparator K serves as a control signal for a switch register SR which directly switches the active channels (online), or the state is conveyed to the computer via an additional connection V in order to make an individual selection of active channels (offline). The output signal of the switch register SR is fed directly to another amplifier A1 for level matching for the subsequent analog-to-digital conversion AD. The A-D-converted values, i.e., the spectrally resolved fluorescence signal of the sample measured in every image point, are transferred via a suitable data line to a computer (PC or digital signal processor DSP) for data processing. Subsequently, depending on the scan mode, lambda stacks (spectral distribution per sample point, measured by the detection channels with dispersive splitting of detected radiation stored in storage elements with allocation to at least one additional coordinate: image point [coordinate x,y] and/or Z and/or measurement time t) are formed from the individual image points that are measured in a spectrally resolved manner with the additional coordinates x, y, z, time and lifetime, where X and Y are scanned by SC;

Z is carried out, for example, by displacing the preparation along the optical axis;

Time: the data acquisition is carried out at different times;

Lifetime: the data recording is carried out in a time-resolved manner within the fluorescence lifetime.

In fluorescence measurement, it is useful for prevention of artifacts to suppress the excitation light scattered from the sample or at least to reduce it to the extent that its intensity it is less than, or on the same order of magnitude as, the emission maximum. For this purpose, the additional line filter, described above, or a correspondingly optimized main color filter (MDB) can be used for optical attenuation. Alternatively, an AOTF can be used as main color splitter as is described in DE19859314 A1 or DE 19842288 A1. Since the spectral width of the excitation laser radiation is very much smaller than the bandwidth detected by the individual channel, the backscattered or reflected excitation radiation can also be effected by deliberately switching off the corresponding individual channel with the SR shown in FIG. 6. When the excitation wavelength strikes two detection channels, the excitation line can be shifted in such a way that it only strikes one detection channel by means of a rotation of the grating, a displacement of the line detector or a tilting of S1 or S2 in FIG. 5.

In the arrangements described above, an integrator circuit was preferably used for detecting the individual channel signals. However, a photon count can also take place in the individual channels and the photon numbers can be added, without any limitation. The counted photons can be summed subsequently. An APD (avalanche photodiodes) line would preferably be used as a detector for this purpose.

Various methods for displaying the information of the sample, i.e., the lambda stacks, are described in the following.

By means of the methods described above for recording lambda stacks, a stack of x-y images is obtained which contain the fluorescence intensity values from adjacent, very narrow wavelength regions. More complex data are obtained by combining the recording of these lambda stacks with z-stacks and/or time series.

These data can be prepared in different ways:

a) Lambda maximum projection: In this case, a grayscale image is generated from the lambda stack in that the maximum intensity value which defines the brightness of the corresponding pixel of the projection image is determined for every x-y pixel position over the wavelength regions.

b) Lambda coded projection: In this case, as in a), a lambda maximum projection is calculated and every pixel is provided with the color which corresponds to the average wavelength of the wavelength region from which the brightest pixel of the lambda stack originates.

c) Gallery view for a simple lambda stack (xyλ): In this case, the individual images of the lambda stack are displayed at least partially in a series. For this purpose, the average wavelength of the region in which the intensities were recorded can be indicated for every image.

d) Gallery view for more complex lambda stacks: When xy-lambda stacks are recorded over z and/or over time, slides can be used in order to allow the respective series of a z-plane or time point to be shown in the gallery. In another way, all xy-images of the recording can be displayed simultaneously in that the images differing in spectra are shown in rows and the images differing with respect to time or in the z-plane are shown in columns. The following gallery views can be selected: xy-λ, xy-z, xy-t, xy-λ-z, xy-λ-t, xy-z-t. The dimensions not mentioned can be scrolled through by means of slides.

Simultaneous display of xy-z-t-λ information is made possible by combining the lambda maximum projection or lambda coded projection with the gallery view in rows and columns.

e) Orthogonal sections though lambda stacks: This display shows a selected λ-plane of a lambda stack with a horizontal marking line and a vertical marking line which can be positioned freely. The lambda stack is averaged at these lines and the resulting section image adjacent to (y-section) and along (x-section) the λ-plane is projected. A pseudo true-color coding can be carried out optionally. In so doing, each wavelength region is assigned its corresponding spectral color. A true-color imaging of the sample results by superimposing the individual color components in an image.

Definition of Reference Spectra by Means of ROIs

Reference spectra are, e.g., the emission spectra of individual dyes in their purest form or under sample conditions, i.e., dissolved in solvent or bonded to sample structures in individual discrete regions of the sample to be analyzed. The selection of image regions for generating the reference spectra can be carried out by the following methods by defining regions of interest (ROI).

Figure 7:
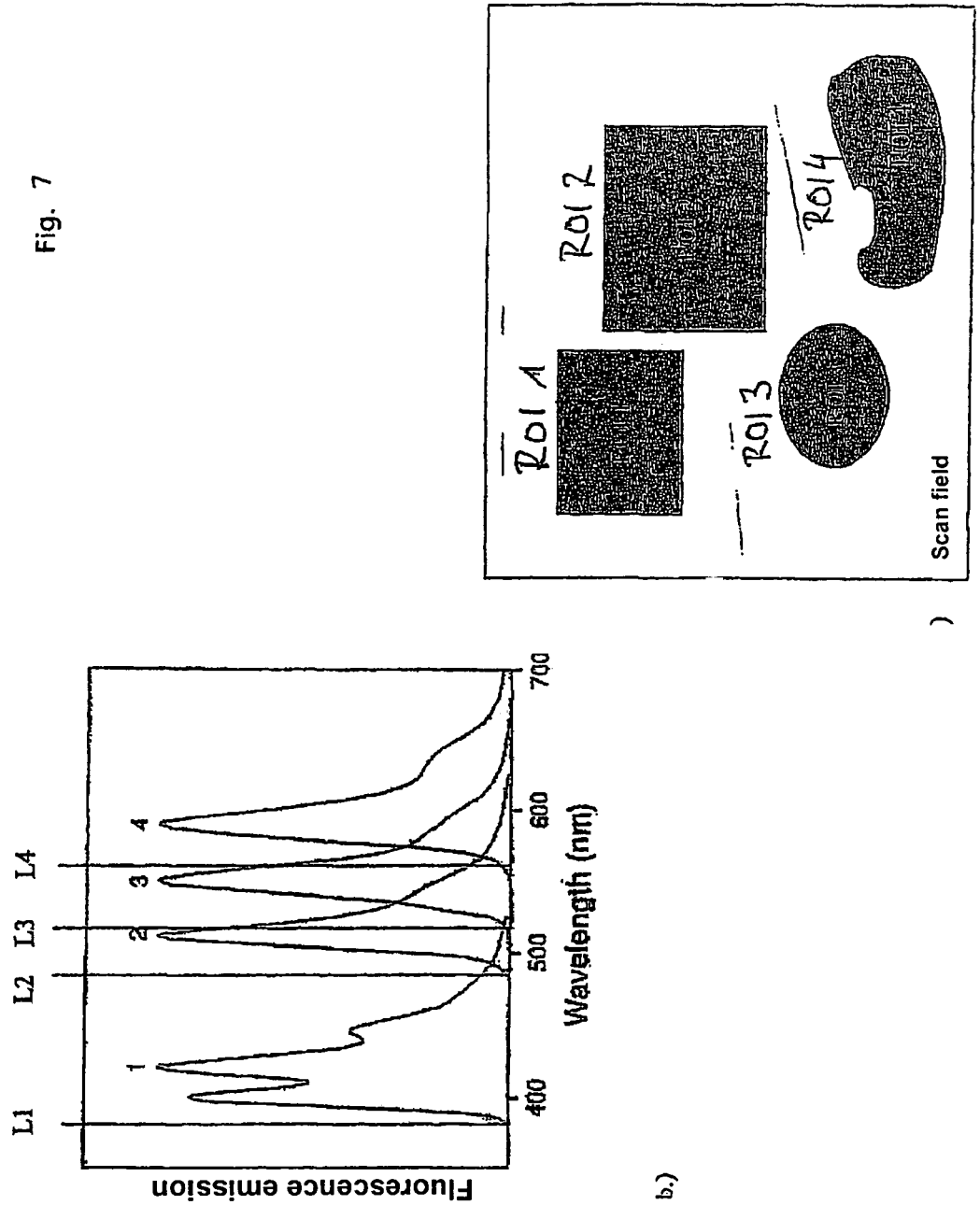
FIG. 7a schematically shows a distribution of different regions of interest (ROIs) in an LSM image which represent, e.g., different dyed regions of a sample.
FIG. 7b shows typical associated emission spectra with their excited wavelengths.

Lambda stacks contain the spectral information for each pixel, in addition. FIG. 7a schematically shows a distribution of different ROIs (ROI 1-4) in an LSM image which represent, e.g., different dyed regions of a sample. Typical associated emission spectra 1-4 are shown with their excitation wavelengths (L1-L4) in FIG. 7b. The user can adjust the ROIs as follows, for example: After a lambda stack is recorded using all or most of the excitation lines needed for exciting the dyes in the individual ROIs, sum channels can be formed between the individual excitation laser lines (L1 to L2, L2 to L3, L3 to L4 and L4, according to FIG. 6, up to the maximum emission wavelength). These sum channels correspond to parts of the fluorescence bands of the individual dyes. Further, a simultaneous summation of the signals of different dyes is carried out in the same sum channels because of the extensive overlapping. These sum channels are subsequently stored in different image channels in a color-coded manner and are shown superimposed on one another. Because of the different local color mixing in the image channels, the different ROIs can be localized by the user or by automatic pattern recognition.

In a second method for adjusting the different ROIs, the fluorescence centroid is measured (DE10033180A1). For this purpose, all individual channels that are irradiated with excitation laser lines are switched off in the detector. Every ROI has a characteristic fluorescence centroid because of the changed emission characteristics of the respective dyes that are used. The different ROIs can accordingly be distinguished by the position of the characteristic color centroid and made visible separately.

The user can use the ROI function (ROI=Region Of Interest; see FIG. 8) to make visible the spectral signatures of any selected sample locations. In so doing, a region (ROI 1 and ROI 2 in FIG. 8) of a recorded sample is marked in image 2 with a marking tool 3 (e.g., polygon, ellipse or closed spline) and the graph of the corresponding spectral signature is determined (diagram 1) by taking the average of the x-y pixels enclosed in the ROI for every λ-plane of the lambda stack.

In principle, a plurality of spectral signatures of different selected sample locations can be displayed simultaneously either in a common or separate diagrams 1.

The visualized spectral signatures 1 give information about the spectral distribution of the fluorescence emission in the selected sample locations. When a plurality of spectral signatures of different ROIs are displayed, it can be determined, for example, whether or not the emission spectra of the dyes overlap significantly.

Figure 8:
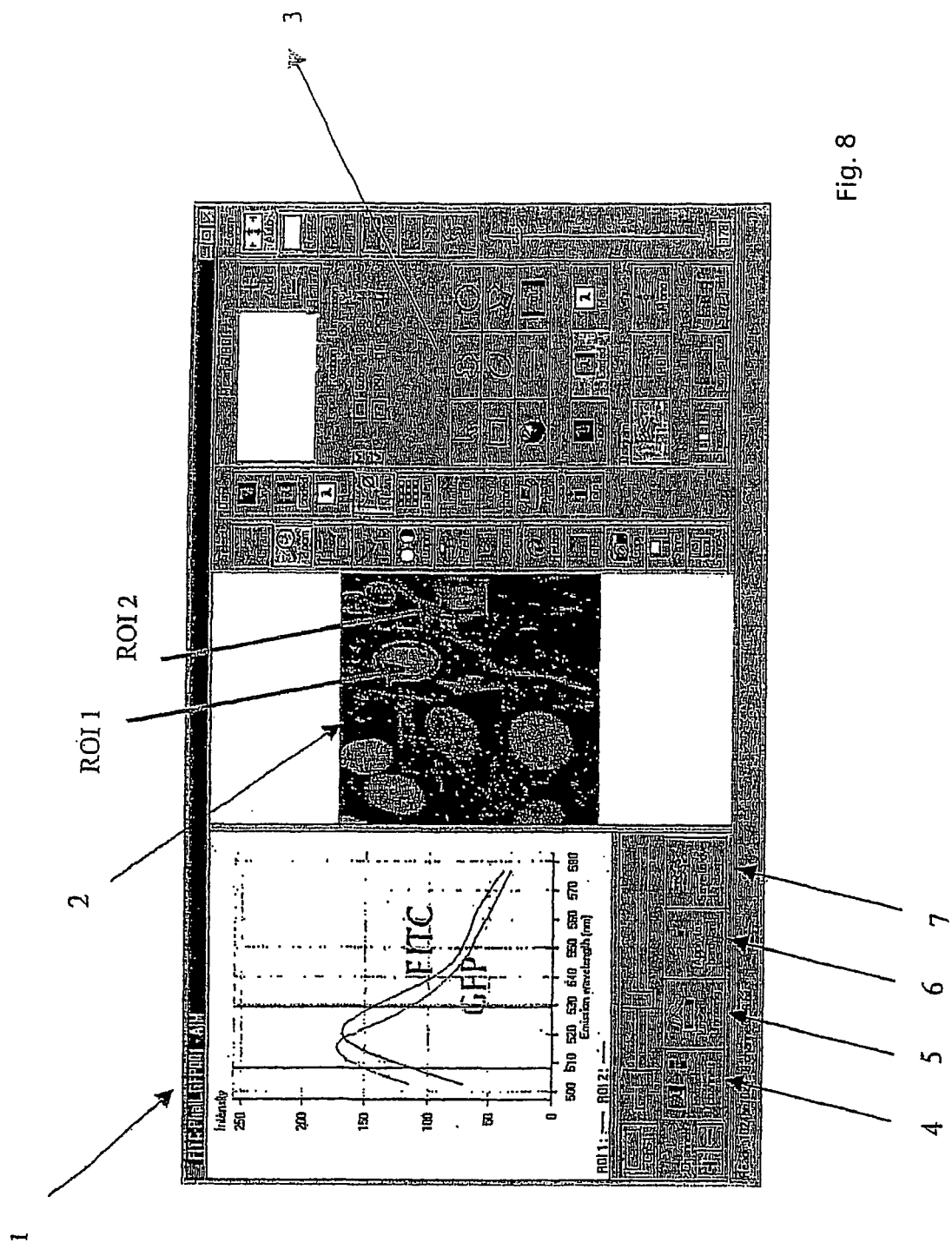
FIG. 8 shows how the user can use the POI function to make visible the spectral signatures of any selected sample locations.

As is shown in FIG. 9, the spectral signatures of the different ROIs can be used to generate a color-coded multichannel image ("extract to channels" operating control, FIG. 8, No. 4. Wavelength regions can be selected (FIG. 9a: ROIs 1 to 5) by means of the spectral signatures and the intensity values of the corresponding planes of the lambda stack can be combined, e.g., by summation or averaging over the corresponding wavelength regions for every image point, in order to generate a multichannel image (FIG. 9b), wherein every image channel represents a dye (Ch 1 to CH 5)).

In addition, this adjustment can be used for electronic summation (see FIG. 6) of the individual channels ("extract to hardware", FIG. 8, No. 6). Subsequently, multichannel images can be directly scanned with the corresponding adjustments.

The spectral signatures of individual ROIs, i.e., individual dyes in their specific environment, can be stored in a spectral database (FIG. 8, No. 7) for subsequent reuse; in addition to the data of the graphs, the parameters specific to the recording of the lambda stack, such as the laser lines, intensities, filter configurations (MDB, NFT, EF) and adjustment of the detector (gain, integration time, pinhole position and pinhole diameter) and additional comments on the environment and/or preparation of the sample to be analyzed can also be stored.

When the lambda stack is recorded over a period of time, spectral signatures can be determined at different times and combined in a series. Subsequently, these data can be visualized in a three-dimensional display, e.g., corresponding to FIG. 10, and the change in the spectral signatures over time in different ROIs can be conveyed. In an advantageous manner, this display can be used with two or more fluorescence dyes simultaneously during the evaluation of experiments such as FRET (Fluorescence Resonance Energy Transfer) or FRAP (Fluorescence Recovery After Photobleaching) (see FIG. 10). Drawing part b shows the fluorescence signal (intensity) as a function of wavelength and time. It will be seen that the signal in the wavelength range of 530 nm to 560 nm increases with time. Another type of display is shown in FIG. 13a. The spectral individual channels are shown at different points in time. Every drawing part represents a wavelength range of 10 nm, for example.

Algorithms for analysis, e.g., for selective display of the contributors of individual dyes to the total fluorescence signal radiated from the sample are described in the following. The analysis can be carried out quantitatively or qualitatively. In a quantitative analysis, the contribution (i.e., concentration) of every individual dye to the total fluorescence signal radiated from the sample is calculated for every image point. Algorithms such as, e.g., a linear unmixing analysis (Lansford, et al., Journal of Biomedical Optics 6(3), 311-318, (July 2001)) are used. Reference spectra, as they are called, are needed for the analysis. These reference spectra describe the fluorescence spectrum of an individual dye. The accuracy of the results depends decisively on the accuracy of the reference spectra. Therefore, in a method according to the invention, the reference spectra are recorded simultaneously while examining the preparation (see below). The contributions of the respective dyes are collated in different image channels and a specific color is allocated to every image channel. The brightness of the color is determined by the size of the contribution. Subsequently, the individual image channels can be displayed superimposed in an image and a color-coded (lambda-coded) image results.

In a qualitative analysis, a classification is carried out, i.e., only the dye generating the greatest contribution to the total fluorescence signal radiated by the sample is allocated to every image point. The allocation is carried out again in an image in different image channels and a specific color can be allocated to every image channel. Algorithms such as *principal component analysis* (PCA, I. T. Joliffe, Principal Component Analysis, Springer-Verlag, New York, 1986) are used for this purpose. Through this type of algorithm, a masking of the image (dye mask) is obtained, wherein identical dyes are located in regions of the same color.

Method steps for separating dye fluorescences will be described in the following.

When the spectral signatures of the selected ROIs represent only the emission signal of exactly one of the utilized dyes in the sample (reference spectra), they can be used in a particularly advantageous manner for a quantitative analysis (e.g., digital unmixing, Fig. (No. 5) of the emission signals (FIG. 12a). The input data for this are the lambda stack, upon which the analysis is based, and the spectral signatures of n selected sample locations (ROI), where n is the quantity of dyes used in the sample. The result of the quantitative analysis (e.g., unmixing) is an image comprising n individual image channels, each of which contains only the information of the emission signals of one dye.

Another procedure for quantitative analysis (e.g., digital unmixing) of the emission signals uses, as input data, a lambda stack and reference spectra for the latter which have been stored beforehand in a spectrum database (FIG. 12b). These reference spectra can come from an experiment (calibrating measurement) in which a sample (or specific regions) was marked with only exactly one fluorescence dye. This procedure is required, for example, when the dyes are predominantly co-localized in the actual experiment and, accordingly, a sample location with a pure emission signal without spectral crosstalk of another emission cannot be found for every dye, i.e., no ROI can be marked.

In addition, the reference spectra from the database can be selected by the user before the lambda stack is recorded and a quantitative analysis (e.g., digital unmixing) of the lambda stack can be carried out immediately during acquisition. As a result, the image of n-channels is displayed on the screen. A memory-intensive buffer storage of the lambda stack data can be dispensed with in this case.

Figure 11:
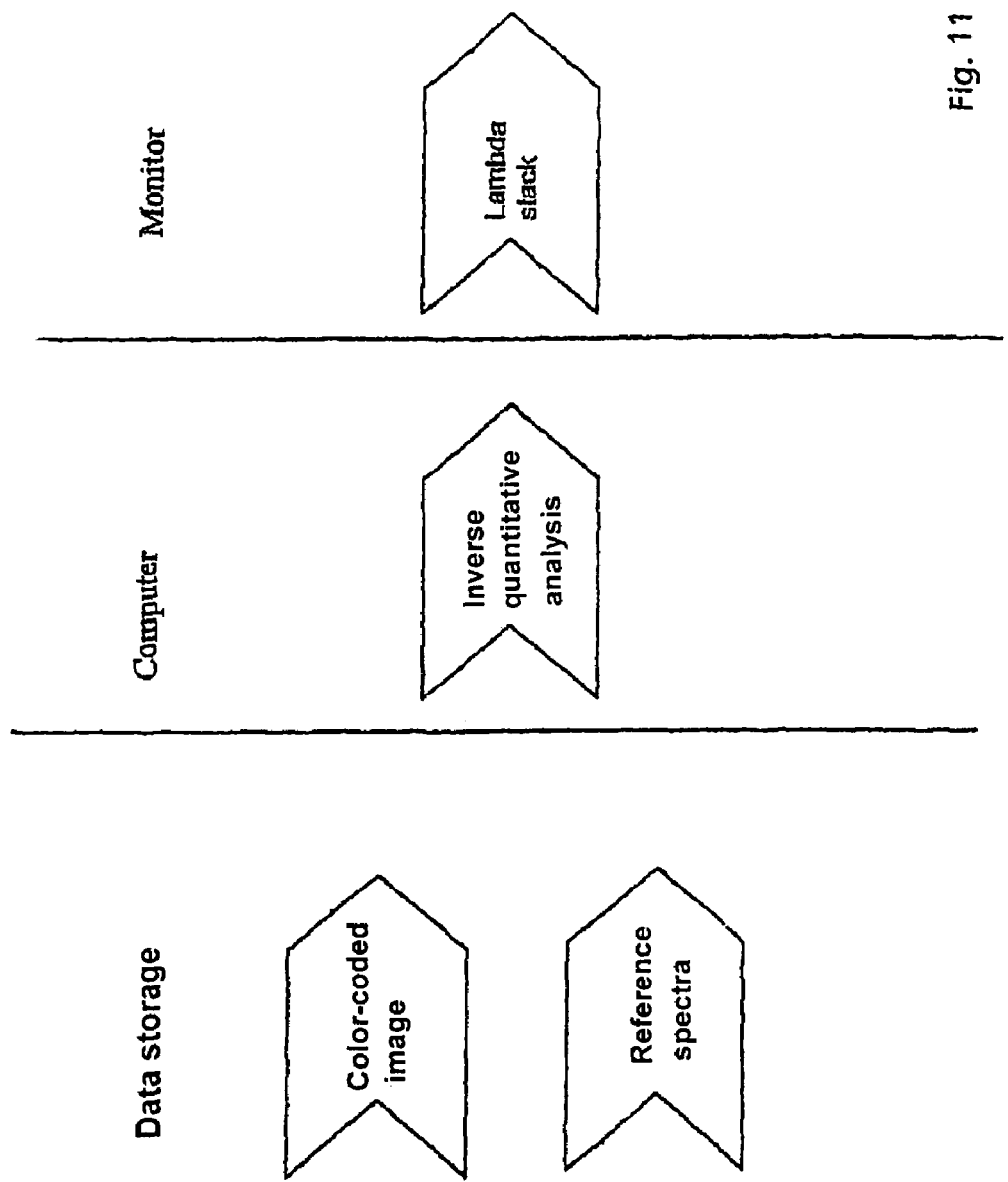
FIG. 11 schematically illustrates quantitative analysis of data sets and the reference spectra.

In another method which is shown schematically in FIG. 11, quantitatively analyzed data sets (color-coded image) and the reference spectra, in accordance with the quantity of dyes, are stored on a data medium instead of the lambda stack. This has the advantage that the size of the data set can be stored without a serious loss of signal information. For example, when a lambda stack with 32 individual channels in 512×512 image points and 8 bits is detected, the size of the image stack is approximately 16 megabytes. By storing the color-coded image, the size of the data set is reduced by a factor of 32 to approximately 0.5 megabytes, plus the reference spectra. The quantity of data points in the reference spectra is 32 multiplied by the quantity of dyes. The lambda stack can be calculated again subsequently in the computer from the stored data (reference spectra) and color-coded image. In the simplest case, the calculation is carried out by multiplying the reference spectra by the respective image channels of the color-coded image. Data reduction is necessary particularly when time series or time series with three-dimensional image information are recorded.

In another method whose flowchart is shown in FIG. 12c, a qualitative analysis is carried out in the first step starting from the lambda stack. On the one hand, areas in the preparation in which identical dyes are spatially distributed can be found through this analysis. On the other hand, the reference spectra required for the subsequent quantitative analysis can be generated automatically without user intervention. Apart from the lambda stack, no additional input parameters are needed for the qualitative analysis, e.g., PCA. The reference spectra obtained in this way and the lambda stack are then used as input parameters for a quantitative analysis, which again results in a color-coded image.

In another method according to FIG. 12D, a limited qualitative analysis of the lambda stack is carried out. In the limited qualitative analysis, only spectra that have been defined by the user beforehand and stored, e.g., in a dye database, are used.

The algorithm searches these predefined dye spectra for the instances (i.e., dyes) that most closely match the fluorescence signal measured in a spectrally resolved manner and accordingly defines the reference spectra. The reference spectra obtained in this way and the lambda stack are then used as input parameters for a quantitative analysis, which again results in a color-coded image.

Figure 12:
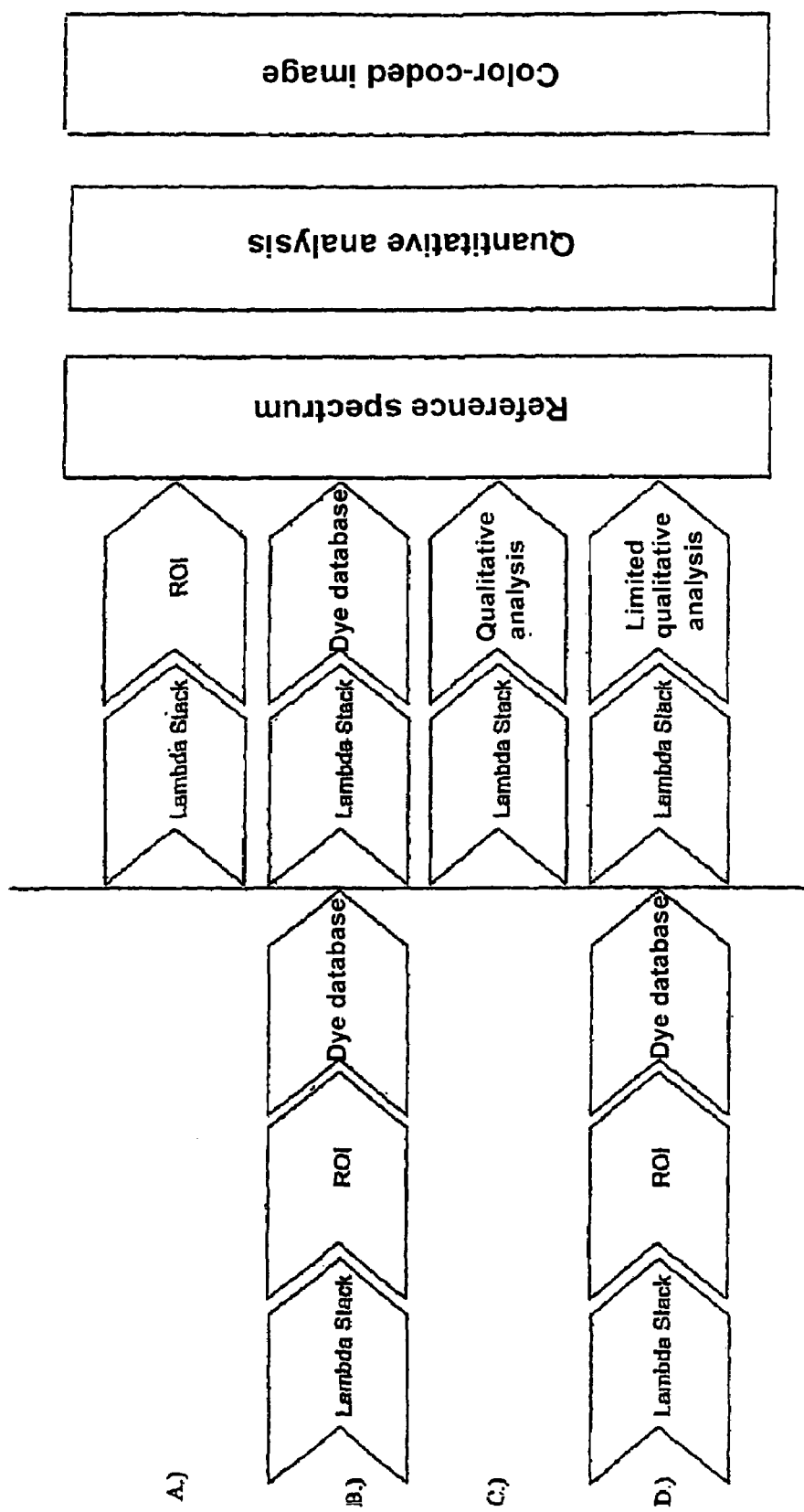
FIG. 12a illustrates quantitative analysis, e.g., digital unmixing of the emission signals.
FIG. 12b illustrates another procedure for quantitative analysis, e.g., digital unmixing of the emission signals.
FIG. 12c illustrates a flow chart of yet another method of quantitative analysis.
FIG. 12d illustrates yet another method where limited quantitative analysis of the lambda stack is carried out.
Figure 13:
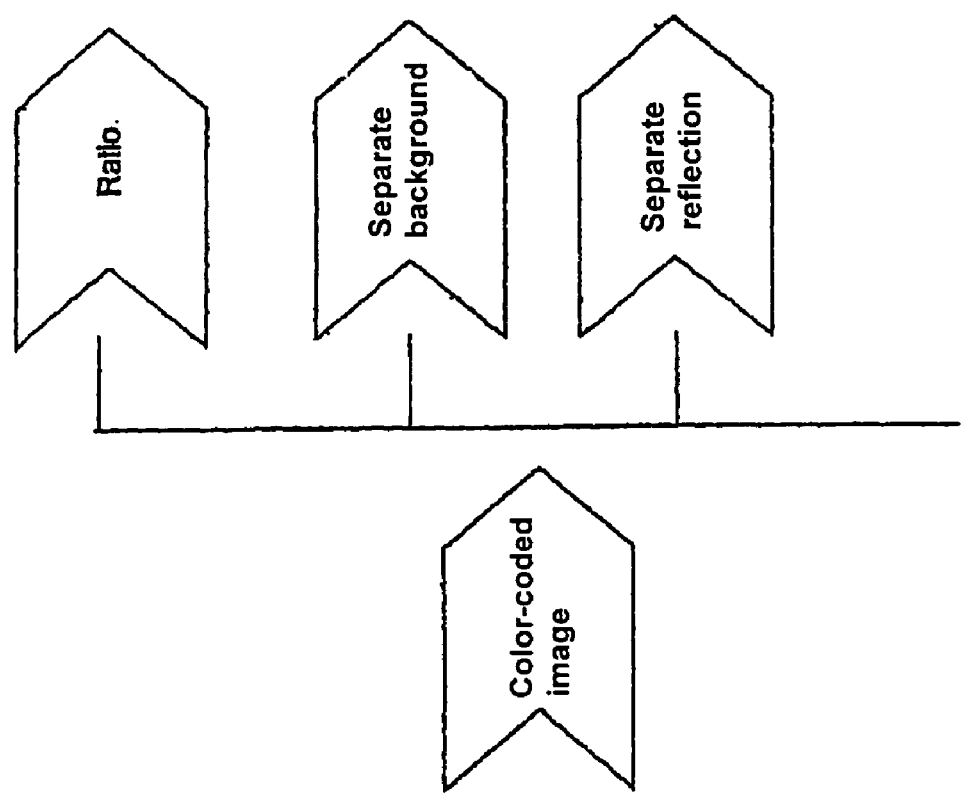
FIG. 13 illustrates a display where the spectral individual channels are shown at different points in time.

Another application of the methods described above consists in the separation of signals which are not relevant for the respective investigation or which interfere with the analysis. These signals can be, e.g., background light, autofluorescence, backscattered excitation light or room light. When the spectral distribution of these signals is initially determined in control preparations which are not further dyed (autofluorescence, backscattered excitation light) or in the absence of the preparations (background light, room light), the obtained spectra can be included in the linear unmixing analysis like the reference spectra of the dyes to be investigated (FIGS. 12 and 13). After unmixing, they are accordingly allocated to a separate image channel and separated from the signals to be investigated which can accordingly be observed separately.

Explanation of Terminology:

$\lambda$-Stack: Spectral distribution per image point, measured by the detection channels with dispersive splitting of the detected radiation, stored in storage elements by allocation to at least one additional (image point) coordinate x,y and/or Z and/or measurement time t.

Quantitative analysis: The contribution (proportion) of each spectral signature to the total signal (e.g., fluorescence signal) coming from the sample is calculated for every image point (unmixing method). The calculation is carried out based on reference spectra which characterize the spectrum of the individual spectral signatures (e.g., dyes) and which have been stored in a database, generated from the image (ROI) or generated by qualitative analysis (PCA).

Image channels: A color is assigned to every selected spectral region when displaying the sample as an image (false color display), wherein the intensity of the color corresponds to the contribution of the dye/spectral signature, measured, for example, in a plurality of detection channels through corresponding filters.

A color-coded image (mixed image) is formed by the graphic display of a plurality of colors when a plurality of spectral signatures/dyes are contained in a sample region.

Qualitative analysis: The spectral signature/dye which generates the greatest contribution of the total signal coming from the sample is assigned to every image point.

Dye mask: Spectral signatures/dyes at different locations are displayed with different colors, with uniform intensity in each instance.

ROI: Regions which are found and marked by the user; regions with identical spectral signatures/dyes can also be found and marked automatically by qualitative analysis.

Applications of the Above-Described Detection Methods for Identifying Spectral Signatures of Multiply-Labeled Objects 1) Production of the Samples In a first step, the samples to be examined are labeled, in accordance with their specific characteristics, with a plurality of dyes. These samples may be, e.g., chromosomes that were dyed by means of the FISH (Fluorescence in situ Hybridization) technique. Cells or tissue can likewise be dyed using fluorescence techniques (e.g., immunocyto- and immunohistochemical dyes). The biologically relevant information in the samples is coded by means of these dyeing techniques.

2) Informational Content of the Samples

In the simplest case, the sample is spatially one-dimensional from the perspective of the detection system (e.g., flow cytometer). Accordingly, the information contained in the sample is coded exclusively by the proportional combination of different dyes (FIG. 14). The structural features S1, S2 and S3 were labeled by dyes A, B and C. Dyes can be distinguished based on their characteristic absorption spectra or emission spectra. Therefore, the identification of a spectrum (spectral signature) makes it possible to draw conclusions about the presence of a determined structural feature.

The samples to be examined are distinguished from one another with respect to the occurrence of the above-mentioned structural features. Sample classes can be defined depending on the occurrence of the combinations of structural features. The individual sample classes are spectrally coded in different ways by the combination of labels.

Figure 15:
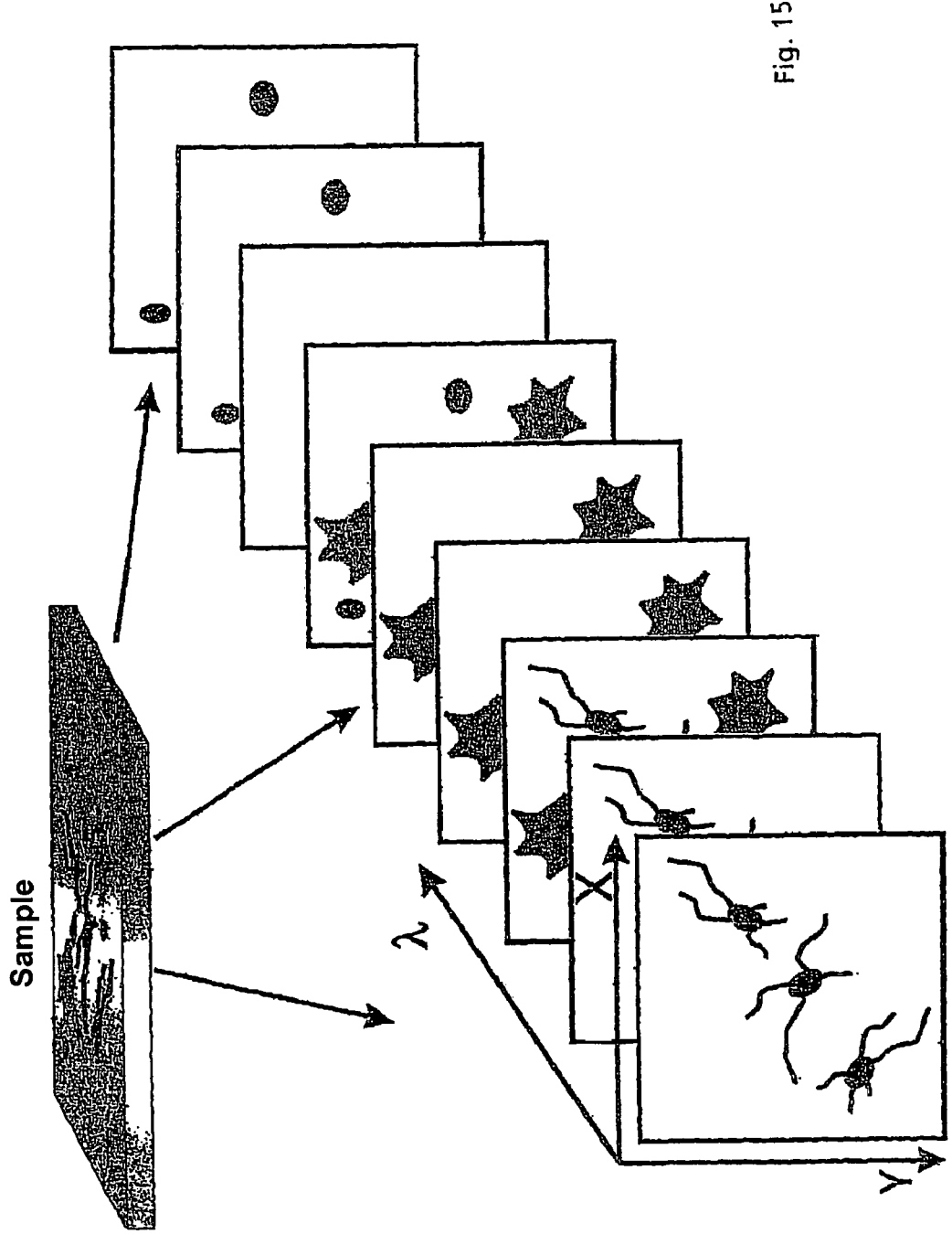
FIG. 15 shows a two-dimensional sample in which three different structures were labelled.

When systems allowing two-dimensional or three-dimensional spatial resolution are used for detection, the informational content that can be detected is considerably increased. The quantity of possible classes increases in that structural features of the sample can occur at different locations. The illustration (FIG. 15) shows a two-dimensional sample in which three different structures were labeled. For the sake of simplicity, only the labels have been shown and not the structures themselves. Sample classes can now be defined means of the two-dimensional or three-dimensional arrangement of the different combinations of structural features. The fact that the different markings can occur with different intensities (concentrations of the structures on the sample plane) provides another parameter that can be used for classification.

3) Detection and Classification

The samples are advantageously examined and evaluated in seven steps:

Step 1

Recording of Lambda Stacks

The samples are examined by the detector described above (reference). In so doing, the individual image points measured in a spectrally resolved manner result in lambda stacks, i.e., spectral distributions per sample point, stored in storage elements so as to be associated with at least one additional coordinate: image point [coordinate x,y] and/or Z and/or measurement time t.

Step 2

Detection of the Reference Spectra of the Utilized Dyes Under Sample Conditions

Reference spectra are, for example, the emission spectra of individual dyes under sample conditions, i.e., dissolved in a solvent or bonded to structures. They are defined based on lambda stacks. These lambda stacks are spectral distributions per sample point, stored in storage elements so as to be associated with at least one additional coordinate: image point [coordinate x,y] and/or Z and/or measurement time t.

Essentially three methods can be used for this purpose. For one, the reference spectra can be obtained from samples, each of which has been labeled by only one dye. Each sample supplies only one spectrum. The reference spectra obtained in this way can be stored in a spectral reference database for future use. This method can be applied particularly in flow cytometry, laser scanning microscopy, total internal reflection fluorescence microscopy (TIRF) and nearfield microscopy.

In another method, it is possible to use multiply-labeled (reference) samples to obtain reference spectra when it is possible to define sample regions that have each been labeled by only one dye.

The selection of such regions for generating reference spectra can be carried out by defining regions of interest (as was described above). Such regions can also be defined by means of algorithms for automatic detection of two-dimensional or three-dimensional objects. This procedure is applicable in systems which detect spatially resolved sample information. Such systems include, for example, laser scanning microscopy, total internal reflection fluorescence microscopy (TIRF) and nearfield microscopy.

A third possibility for generating the reference spectra is principle component analysis (PCA). In this method, lambda stacks or multiply-labeled (reference) samples are recorded with the detector described above. The application of PCA to these data supplies the reference spectra.

Step 3

Figure 20:
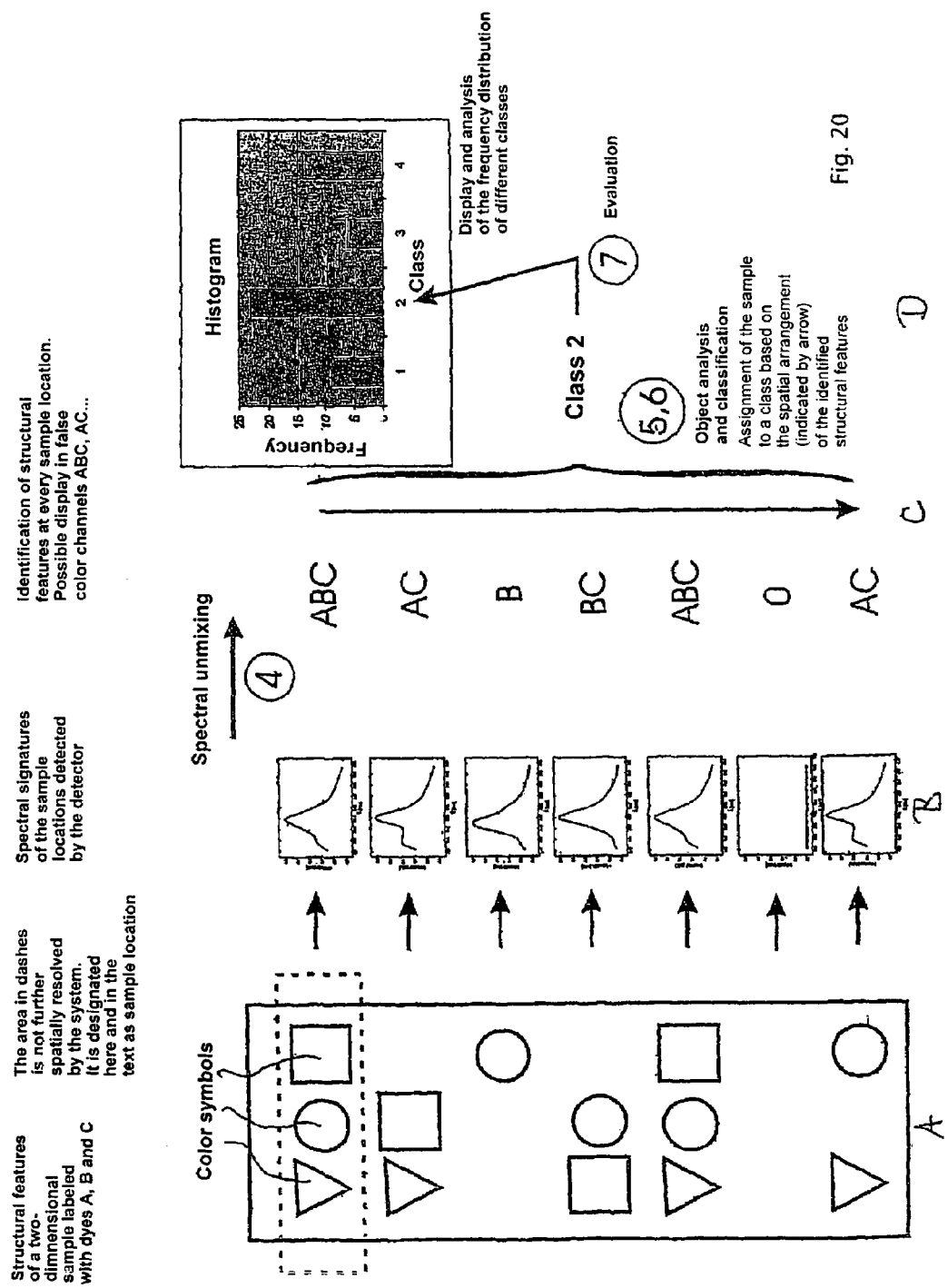
FIG. 20 illustrates an example of object analysis in accordance with the invention.

Object Recognition (FIG. 20A)

Methods employing image analysis (binarization, segmentation) are used to select the elements of the sample (cells, cell components, e.g., tumor cells, chromosomes—shown schematically in FIG. 16A) to be examined. Dye-labeled round tumor cells are selected, for example, based on shape.

Figure 16:
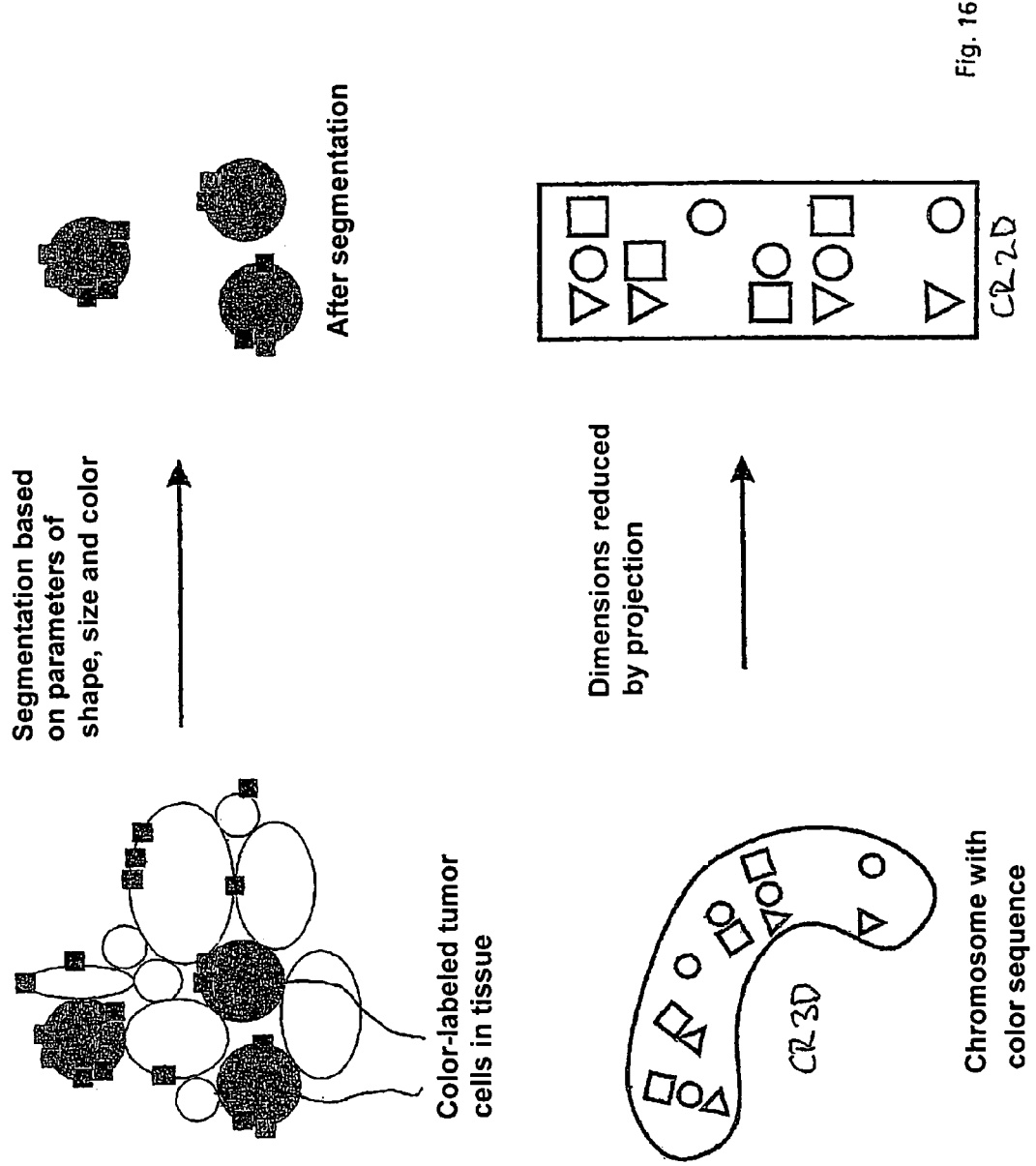
FIG. 16 shows a method employing image analysis to select the elements of the sample.

When multi-dimensional objects are to be detected, projections in systems with fewer dimensions are necessary. Accordingly, a chromosome CR 3D extending in three dimensions in the cell nucleus can first be defined as a cohesive object and subsequently projected in a two-dimensional image for further analysis (FIG. 16B). The different geometric shapes shown in FIG. 16 (triangle, circle, square) correspond to different markers.

Step 4

Unmixing (FIGS. 20B,C)

Figure 17:
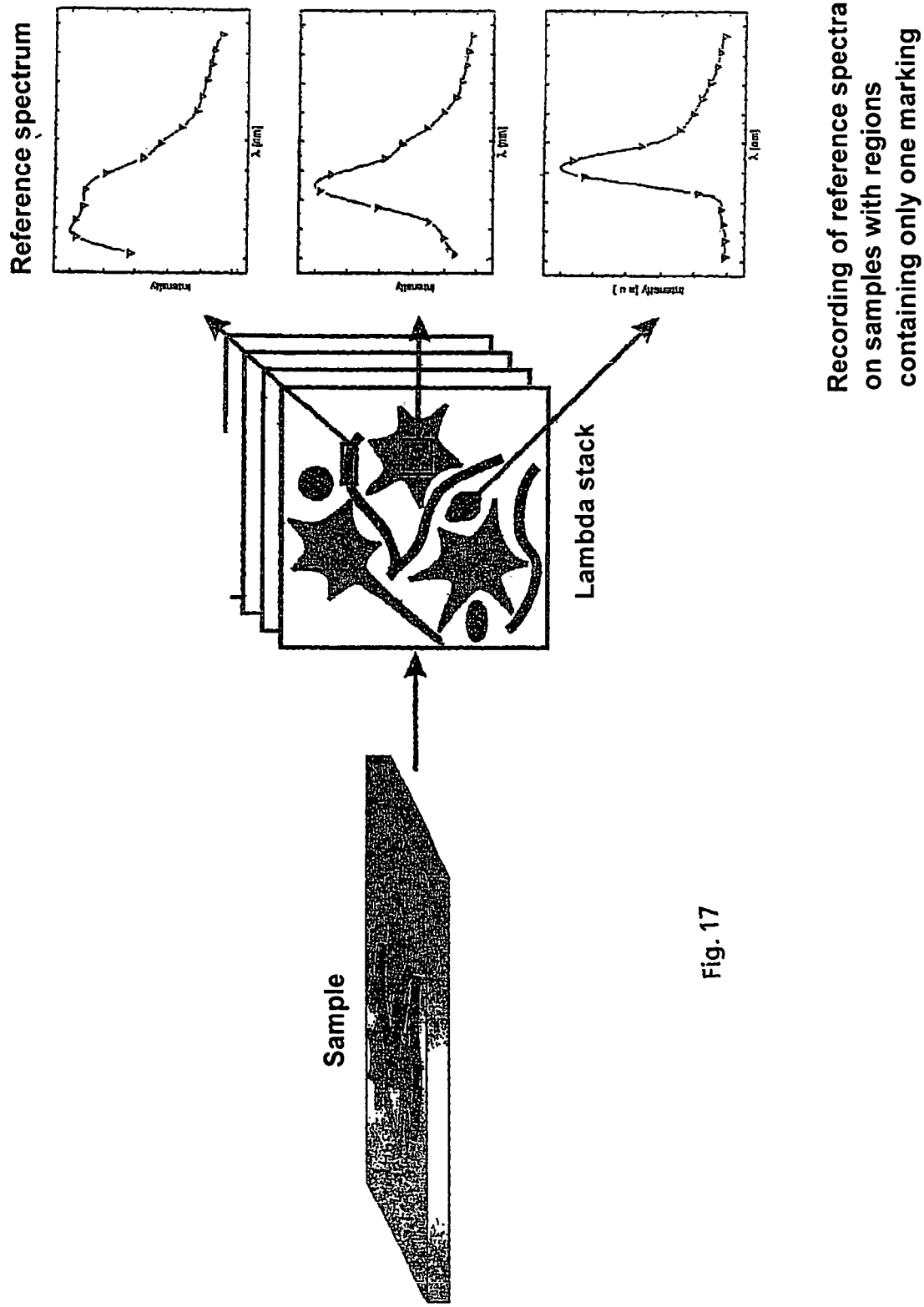
FIG. 17 shows how regions in the sample to be examined that are labelled in each instance by only one dye, the sample itself can be used to generate the reference spectra.

The object of this step is to generate multichannel images of multiply-labeled samples. It is crucially important in this step that it is possible with this method to associate the entire emission signal of one of these dyes to exactly one false color channel. The emission signals can overlap extensively. Two methods can be applied for generating the multichannel images:

1) If there are regions, B1, B2, B3 in FIG. 17, in the sample to be examined that are labeled in each instance by only one dye, the sample itself can be used to generate the reference spectra (see above). On the basis of the reference spectra defined in this way, the multichannel image can be generated by applying linear unmixing (Lansford, et al., Journal of Biomedical Optics 6(3), 311-318, (July 2001) to the lambda stack of the sample.

Figure 18:
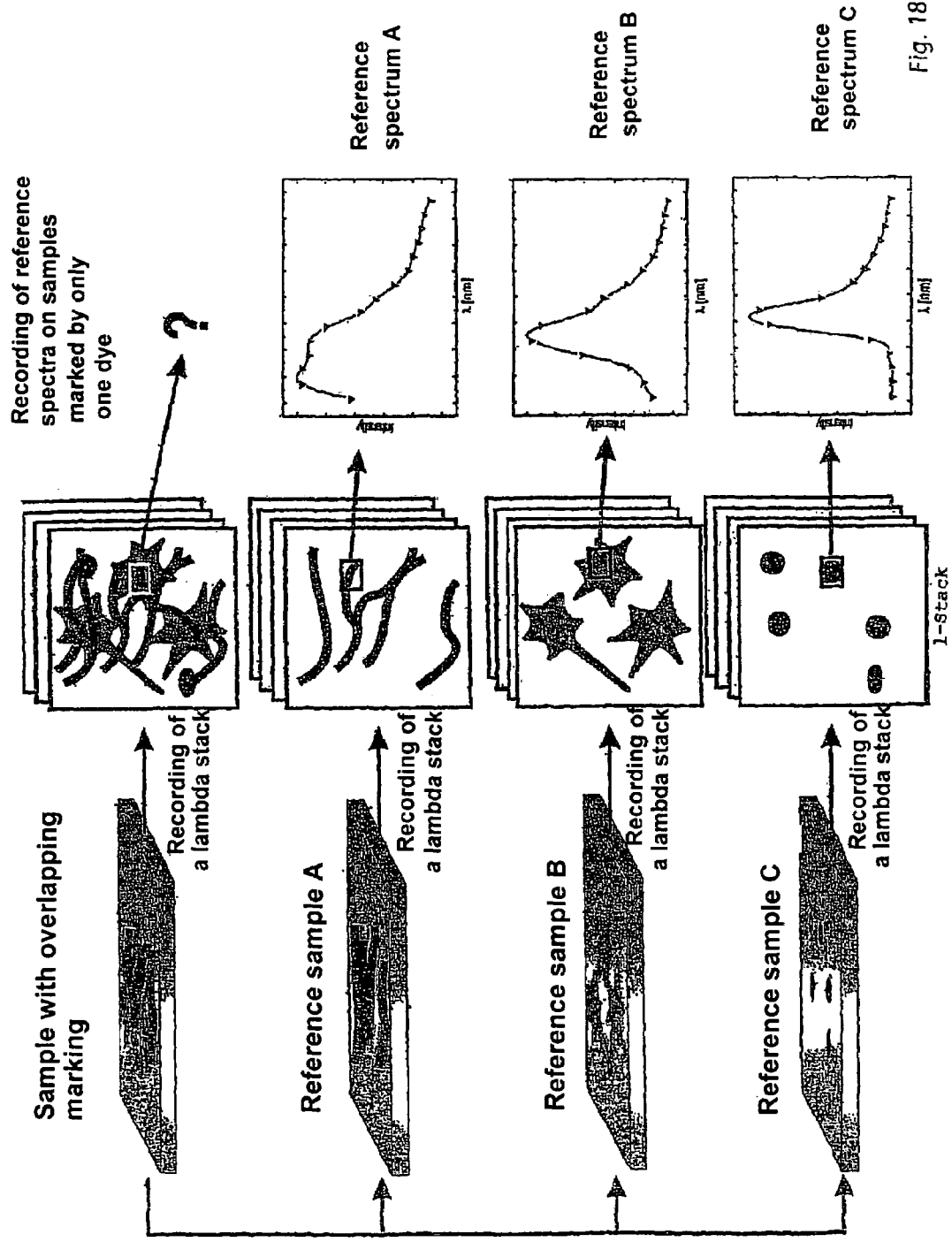
FIG. 18 illustrates how if no regions that are marked with only one dye can be defined in the sample, reference samples which are each marked with one dye can be used to generate the reference spectra.

2) If no regions that are marked with only one dye can be defined in the sample (FIG. 18), reference samples which are each marked with one dye can be used to generate the reference spectra. The reference spectra defined in this way are stored in a spectral reference database, as was described above, and used for linear unmixing of the sample data (lambda stacks). This results in a false color coded multichannel image.

3) Interfering background signals (e.g., autofluorescence and scatter light) can likewise be spectrally characterized. This means that a reference spectrum is also associated with the background signal. When the reference spectrum of the background signal is taken into account in the linear unmixing, a false color coded multichannel image results in which a channel represents the background signal. The multichannel image background can be corrected by masking out the background signal. Alternatively, additional information about the sample can be obtained from the background signal.

4) As an alternative to linear unmixing, multichannel images can also be obtained from the lambda stacks by principle component analysis (PCA).

The multichannel false color images obtained in this way contain all of the information of the sample described above. Accordingly, it is possible to draw conclusions about the distribution of the structural features in the sample.

Step 5 Object Analysis (FIGS. 16 and 20C)

In this step, the previously defined objects are analyzed with respect to the distribution of the structural features. For this purpose, the intensities of the false color channels (see Step 4) are measured at different locations on the objects. These locations are selected in such a way that they represent the desired informational content of the sample.

Step 6 Classification

Figure 19:
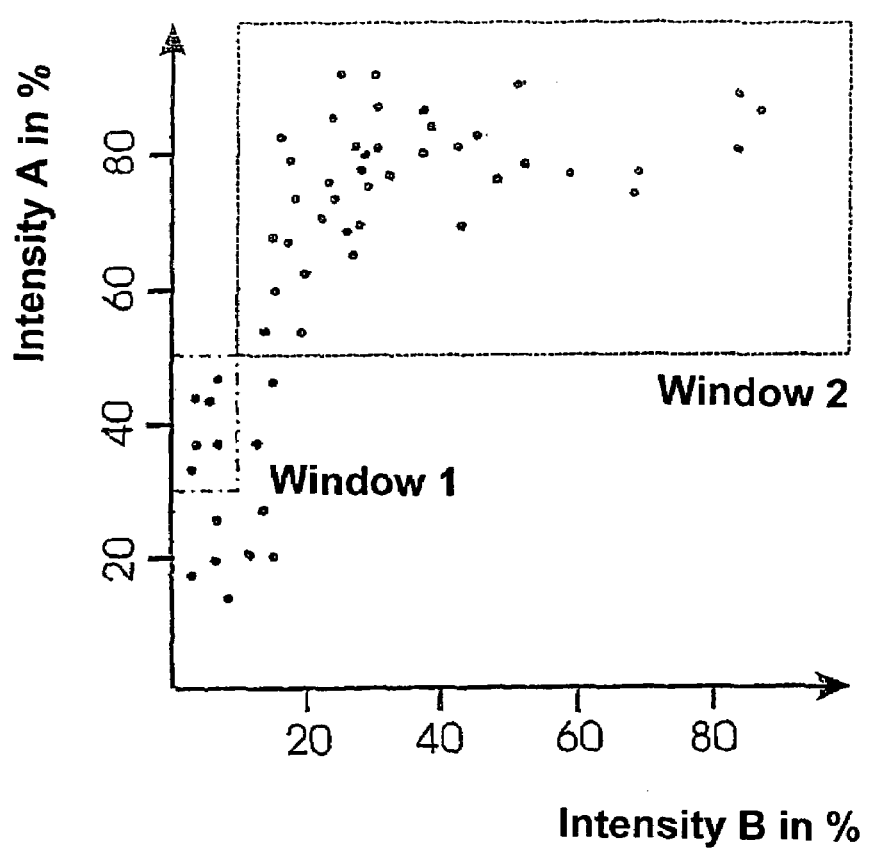
FIG. 19 shows the scatter diagram of a two-channel fluorescent image.

The aim of classification is to distinguish samples based on the distribution of their structural features and to assign them to different classes. A class is defined by the occurrence of a determined combination of structural features in the sample. At least one additional coordinate (image point [coordinate x,y] and/or Z and/or time t), in addition to the spectral information, is used for classification. For example, a scatter diagram can be used to define classes. FIG. 19 shows the scatter diagram of a two-channel fluorescence image. The two axes represent the fluorescence intensities of the image channels. The frequency with which a pixel of the image is assigned to a coordinate of the scatter diagram can be displayed in color coding (blue: few pixels; red: many pixels).

It will be shown in the following based on a double-labeled fluorescence sample how a classification can be carried out by means of scatter diagrams. Reference samples respectively containing only elements of one class are examined first. Two-dimensional scatter diagrams are calculated from the two-channel images of these samples. Each dimension correspondingly represents the fluorescence intensity of a dye. Intensity regions of type F1 (intensity of dye A: 30-50%; intensity of dye B: 0-10%) and F2 (intensity of dye A: 50-100%; intensity of dye B: 30-100%), etc. can then be defined in the scatter diagram by windows of interest (WOI). In so doing, WOIs or combinations of WOIs representing the class-specific characteristics of the samples are defined.

In the next step, the two-channel fluorescence images of the sample to be examined are recorded. Scatter diagrams are calculated from these images. These diagrams are evaluated by means of the previously defined WOIs of the reference scatter diagrams.

It is advantageous to expand the present procedure to more than two dimensions. These dimensions can represent spectral, spatial or dynamic sample characteristics.

The classification can be used to analyze data that were detected with image-generating and analytical microscopy systems. These microscopy systems are image-generating systems such as laser scanning microscopes for three-dimensional observation of biological preparations, nearfield scanning microscopes for high-resolution observation of surfaces, and fluorescence correlation microscopes for quantitative determination of molecule concentrations and diffusion characteristics.

The classification can later be applied to methods based on fluorescence detection such as in systems for screening active ingredients and for flow cytometry. In methods for flow cytometry, the samples (e.g., human cells) can be separated from one another physically according to classification. Naturally, inquiries in which a classification of the samples is not necessary are also conceivable.

Step 7 Evaluation

By means of classification, classes are obtained by which sample characteristics or combinations of sample characteristics are imaged. During evaluation, various questions arise. For example, it may be relevant to know whether or not a sample can be assigned to a known class. When the samples can be assigned to classes, it is generally desirable to know how many samples are to be assigned to a class. This information can be displayed in different ways. Histograms are preferably used for this purpose (see FIG. 20D). The diagram shows the different frequency of allocation to the determined classes.

The method steps described above are summarized in FIG. 20.

The invention is directed particularly to the identification of (preferably) three-dimensional objects based on their spatial extension and spectral signature. The spatial extension can be determined by means of image processing, e.g., from the contrast analysis from a detection channel. At the same time, the lambda stacks are provided at every image point by means of the selected detection arrangement.

In this case, the wavelength-dependent intensity distribution per image point can be determined selectively, i.e., for selected wavelengths or wavelength regions.

Overlapping signals of fluorophores can be separated by unmixing based on reference spectra.

The advantages of the optical and electronic arrangement (parallel acquisition of data, no Fourier transformations as are required in interferometric arrangements, speed) result in a novel quality in screening methods and in the examination of living samples (cell growth) in particular, in the observation of rapidly developing processes, e.g., formal changes in nerve cells, changes in ion concentrations). Accordingly, tumor cells can be detected by their shape, spectrally classified and analyzed with respect to their fluorescence characteristics. Bent chromosomes can advantageously be found, identified and straightened for spectral evaluation, for example. In this case, the samples to be examined can be chromosomes that have been dyed by means of a FISH technique (e.g., multicolor banding). The examined cells, tissue or organisms can be dyed by immunocytological or immunohistochemical dyes.

The methods described above are suitable for medical diagnosis and/or therapy, environmental diagnosis (e.g., water, soil, air) by means of living indicators, diagnosis of tumors, diagnosis and purification of bone marrow cells, and for application in a flow cytometer or an optical nearfield microscope.

While the foregoing description and drawings represent the present invention, invention, it will be obvious to those skilled in the art that various changes may be made therein without departing from the true spirit and scope of the present invention.

The invention claimed is:

1. A method for the analysis of fluorescing samples in an image-generating microscope system, including a laser scanning microscope, comprising the steps of:

scanning a sample point-by-point or line-by-line in at least one surface section;

carrying out dispersive splitting of radiation coming from the sample during the scanning;

detecting the split radiation by at least one line of detector elements in a wavelength-dependent manner;

carrying out a selection of two-dimensional or three-dimensional sample parts which correspond to pre-stored two-dimensional or three-dimensional geometric objects or the like based on recorded and stored intensity distribution of at least one of said detector elements and/or at least one other detector element for the radiation emitted from the sample by image processing;

carrying out an analysis of the spectral signature and/or spatial spectral sequence to produce a result for at least a portion of these sample regions with respect to the fluorescence markers arranged thereon; and providing said result as an output to a user and/or for storage for later use and/or to be displayed by a user; and wherein the time-dependent geometric and/or spectral behavior of the sample regions are/is determined.

2. A method for the analysis of fluorescing samples in an image-generating microscope system, including a laser scanning microscope, comprising the steps of:

scanning a sample point-by-point or line-by-line in at least one surface section;

carrying out dispersive splitting of radiation coming from the sample during the scanning;

detecting the split radiation by at least one line of detector elements in a wavelength-dependent manner;

carrying out a selection of two-dimensional or three-dimensional sample parts which correspond to pre-stored two-dimensional or three-dimensional geometric objects or the like based on recorded and stored intensity distribution of at least one of said detector elements and/or at least one other detector element for the radiation emitted from the sample by image processing;

carrying out an analysis of the spectral signature and/or spatial spectral sequence to produce a result for at least a portion of these sample regions with respect to the fluorescence markers arranged thereon; and providing said result as an output to a user and/or for storage for later use and/or to be displayed by a user; and wherein three-dimensional objects are changed in shape, so as to extend flat over a surface area, prior to the spectral analysis.

3. A method for the analysis of fluorescing samples in an image-generating microscope system, including a laser scanning microscope, comprising the steps of:

scanning a sample point-by-point or line-by-line in at least one surface section;

carrying out dispersive splitting of radiation coming from the sample during the scanning;

detecting the split radiation by at least one line of detector elements in a wavelength-dependent manner;

carrying out a selection of two-dimensional or three-dimensional sample parts which correspond to pre-stored two-dimensional or three-dimensional geometric objects or the like based on recorded and stored intensity distribution of at least one of said detector elements and/or at least one other detector element for the radiation emitted from the sample by image processing;

carrying out an analysis of the spectral signature and/or spatial spectral sequence to produce a result for at least a portion of these sample regions with respect to the fluorescence markers arranged thereon; and providing said result as an output to a user and/or for storage for later use and/or to be displayed by a user; and wherein a determination of the geometric shape is carried out in a plurality of wavelength regions of the detector.

* * * * *